(12) United States Patent
Hancock et al.

(10) Patent No.: US 8,768,485 B2
(45) Date of Patent: Jul. 1, 2014

(54) TISSUE ABLATION APPARATUS AND METHOD OF ABLATING TISSUE

(75) Inventors: Christopher Paul Hancock, Bristol (GB); Mohammad Sabih Chaudhry, Gwyned (GB); Andrew Marc Goodman, Luton (GB)

(73) Assignee: Medical Device Innovations Limited, Cheshire (GB)

( * ) Notice: Subject to any disclaimer, the term of this patent is extended or adjusted under 35 U.S.C. 154(b) by 1190 days.

(21) Appl. No.: 10/536,721

(22) PCT Filed: Nov. 27, 2003

(86) PCT No.: PCT/GB03/05166
§ 371 (c)(1), (2), (4) Date: Oct. 14, 2005

(87) PCT Pub. No.: WO2004/047659
PCT Pub. Date: Jun. 10, 2004

(65) Prior Publication Data
US 2006/0155270 A1    Jul. 13, 2006

(30) Foreign Application Priority Data

Nov. 27, 2002  (GB) .................................. 0227628.5
Nov. 27, 2002  (GB) .................................. 0227635.0

(51) Int. Cl.
*A61F 2/00*    (2006.01)
*A61B 18/04*   (2006.01)
*A61B 18/18*   (2006.01)
*A61B 18/00*   (2006.01)

(52) U.S. Cl.
CPC ....... *A61B 18/18* (2013.01); *A61B 2018/00875* (2013.01); *A61B 2018/00779* (2013.01); *A61B 2018/00869* (2013.01); *A61B 18/1815* (2013.01); *A61B 2018/00702* (2013.01)
USPC ................................ 607/101; 606/33; 606/34

(58) Field of Classification Search
USPC ............ 606/33, 34, 38, 41, 42; 607/106, 107, 607/101
See application file for complete search history.

(56) References Cited

U.S. PATENT DOCUMENTS 4,114,623 A   9/1978  Meinke et al.
4,209,018 A   6/1980  Meinke et al.
(Continued)

FOREIGN PATENT DOCUMENTS

CA    2089739    4/1992
CA    2397340    8/2001
(Continued)

OTHER PUBLICATIONS

JP Search Report Mailed Nov. 1, 2011 in JP Patent Application No. 000657/2010.

*Primary Examiner* — Anhtuan T Nguyen
*Assistant Examiner* — Rynae Boler
(74) *Attorney, Agent, or Firm* — Stites & Harbison PLLC; Douglas E. Jackson

(57) ABSTRACT

An apparatus and method for ablating tissue is disclosed. The apparatus comprises a source of microwave radiation (1), a probe (5) for directing the microwave radiation into tissue, one or more detectors for detecting the power and phase of the microwave radiation and an impedance adjuster (50) for adjusting impedance so as to minimize the amount of microwave radiation which reflected back through the probe. The detector or detectors use a local oscillator (230) to derive the phase information. A modulator for modulating the microwave radiation to a cutting frequency is also disclosed.

36 Claims, 14 Drawing Sheets

(continued)

(56) References Cited

U.S. PATENT DOCUMENTS

| | | | |
|---|---|---|---|
| 4,397,313 A | | 8/1983 | Vaguine |
| 4,488,559 A | | 12/1984 | Berube et al. |
| 4,571,552 A | * | 2/1986 | Brown .................. 330/47 |
| 4,825,880 A | | 5/1989 | Stauffer et al. |
| 4,976,711 A | * | 12/1990 | Parins et al. .................. 606/48 |
| 5,057,105 A | * | 10/1991 | Malone et al. .................. 606/28 |
| 5,057,106 A | | 10/1991 | Kasevich et al. |
| 5,108,391 A | | 4/1992 | Flachenecker et al. |
| 5,113,065 A | * | 5/1992 | Heynau .................. 250/203.2 |
| 5,227,730 A | | 7/1993 | King et al. |
| 5,364,392 A | | 11/1994 | Warner et al. |
| 5,370,678 A | | 12/1994 | Edwards et al. |
| 5,405,346 A | | 4/1995 | Grundy et al. |
| 5,496,271 A | | 3/1996 | Burton et al. |
| 5,507,791 A | | 4/1996 | Sit |
| 5,509,916 A | | 4/1996 | Taylor |
| 5,518,861 A | | 5/1996 | Coveleskie et al. |
| 5,519,359 A | * | 5/1996 | Driscoll .................. 331/39 |
| 5,524,281 A | * | 6/1996 | Bradley et al. .................. 455/67.15 |
| 5,557,283 A | | 9/1996 | Sheen et al. |
| 5,693,082 A | | 12/1997 | Warner et al. |
| 5,704,355 A | * | 1/1998 | Bridges .................. 607/154 |
| 5,713,946 A | | 2/1998 | Ben-Haim |
| 5,720,718 A | | 2/1998 | Rosen et al. |
| 5,749,869 A | | 5/1998 | Lindenmeier et al. |
| 5,807,257 A | | 9/1998 | Bridges |
| 5,810,803 A | | 9/1998 | Moss et al. |
| 5,829,437 A | | 11/1998 | Bridges |
| 5,868,739 A | | 2/1999 | Lindenmeier et al. |
| 5,906,609 A | | 5/1999 | Assa et al. |
| 5,944,749 A | | 8/1999 | Fenn |
| 5,957,969 A | | 9/1999 | Warner et al. |
| 5,991,605 A | * | 11/1999 | Rapeli .................. 455/76 |
| 6,002,968 A | | 12/1999 | Edwards |
| 6,016,811 A | | 1/2000 | Knopp et al. |
| 6,020,795 A | * | 2/2000 | Kim .................. 333/33 |
| 6,026,331 A | | 2/2000 | Feldberg et al. |
| 6,047,215 A | | 4/2000 | McClure et al. |
| 6,148,236 A | | 11/2000 | Dann |
| 6,245,062 B1 | | 6/2001 | Berube et al. |
| 6,251,128 B1 | | 6/2001 | Knopp et al. |
| 6,256,130 B1 | * | 7/2001 | Bulow .................. 398/141 |
| 6,287,302 B1 | | 9/2001 | Berube |
| 6,306,132 B1 | | 10/2001 | Moorman et al. |
| 6,311,090 B1 | | 10/2001 | Knowlton |
| 6,312,427 B1 | | 11/2001 | Berube et al. |
| 6,325,796 B1 | | 12/2001 | Berube et al. |
| 6,334,074 B1 | | 12/2001 | Spertell |
| 6,345,194 B1 | | 2/2002 | Nelson et al. |
| 6,347,251 B1 | | 2/2002 | Deng |
| 6,350,276 B1 | | 2/2002 | Knowlton |
| 6,383,182 B1 | | 5/2002 | Berube et al. |
| 6,413,255 B1 | | 7/2002 | Stern |
| 6,421,550 B1 | | 7/2002 | Bridges et al. |
| 6,448,788 B1 | | 9/2002 | Meaney et al. |
| 6,463,336 B1 | | 10/2002 | Mawhinney |
| 6,470,217 B1 | | 10/2002 | Fenn et al. |
| 6,471,696 B1 | | 10/2002 | Berube et al. |
| 6,477,426 B1 | | 11/2002 | Fenn et al. |
| 6,524,768 B1 | | 2/2003 | Limbach et al. |
| 6,582,426 B2 | | 6/2003 | Moorman et al. |
| 6,635,055 B1 | | 10/2003 | Cronin |
| 6,652,520 B2 | | 11/2003 | Moorman et al. |
| 6,663,622 B1 | | 12/2003 | Foley et al. |
| 6,673,068 B1 | * | 1/2004 | Berube .................. 606/33 |
| 6,684,097 B1 | | 1/2004 | Parel et al. |
| 6,699,237 B2 | | 3/2004 | Weber et al. |
| 6,890,331 B2 | * | 5/2005 | Kristensen .................. 606/34 |
| 7,226,446 B1 | * | 6/2007 | Mody et al. .................. 606/33 |
| 2001/0016762 A1 | | 8/2001 | Carr |
| 2001/0020178 A1 | | 9/2001 | Arndt et al. |
| 2001/0020180 A1 | | 9/2001 | Arndt et al. |
| 2001/0029368 A1 | | 10/2001 | Berube |
| 2001/0034519 A1 | | 10/2001 | Goble et al. |
| 2001/0039416 A1 | | 11/2001 | Moorman et al. |
| 2001/0044643 A1 | | 11/2001 | Litovitz |
| 2002/0022836 A1 | | 2/2002 | Goble et al. |
| 2002/0043326 A1 | | 4/2002 | Bright et al. |
| 2002/0058932 A1 | | 5/2002 | Moorman et al. |
| 2002/0065529 A1 | | 5/2002 | Laurent et al. |
| 2002/0072645 A1 | | 6/2002 | Chornenky et al. |
| 2002/0087151 A1 | | 7/2002 | Mody et al. |
| 2002/0091427 A1 | | 7/2002 | Rappaport et al. |
| 2002/0120261 A1 | | 8/2002 | Morris et al. |
| 2002/0128642 A1 | | 9/2002 | Berube et al. |
| 2002/0133151 A1 | | 9/2002 | Hung et al. |
| 2002/0134779 A1 | | 9/2002 | Furtlehner et al. |
| 2002/0145483 A1 | * | 10/2002 | Bouisse .................. 333/17.3 |
| 2002/0158212 A1 | * | 10/2002 | French et al. .................. 250/459.1 |
| 2002/0165529 A1 | | 11/2002 | Danek |
| 2002/0193783 A1 | | 12/2002 | Gauthier et al. |
| 2002/0193786 A1 | | 12/2002 | Berube et al. |
| 2002/0193849 A1 | | 12/2002 | Fenn et al. |
| 2003/0004454 A1 | | 1/2003 | Fenn et al. |
| 2003/0065317 A1 | | 4/2003 | Rudie et al. |
| 2003/0069575 A1 | | 4/2003 | Chin et al. |
| 2003/0069619 A1 | | 4/2003 | Fenn et al. |
| 2003/0073988 A1 | | 4/2003 | Berube et al. |
| 2003/0195500 A1 | | 10/2003 | Moorman et al. |
| 2004/0064606 A1 | | 4/2004 | Kimura |
| 2004/0071317 A1 | | 4/2004 | Pavlovie et al. |
| 2004/0084748 A1 | | 5/2004 | Park |
| 2006/0273255 A1 | * | 12/2006 | Volkov et al. .................. 250/336.1 |
| 2008/0234574 A1 | * | 9/2008 | Hancock et al. .................. 600/430 |

FOREIGN PATENT DOCUMENTS

| | | |
|---|---|---|
| DE | 3637549 | 5/1988 |
| DE | 60110379 | 6/2005 |
| EP | 0 256 524 | 2/1988 |
| EP | 1 013 228 | 6/2000 |
| EP | 1 080 694 | 7/2001 |
| EP | 1 118 310 | 7/2001 |
| EP | 1 123 135 | 8/2001 |
| EP | 1 186 274 | 3/2002 |
| EP | 1 543 788 | 6/2005 |
| FR | 2617723 | 1/1989 |
| GB | 1 126 901 | 4/1984 |
| JP | 6076962 | 3/1994 |
| JP | 6119265 | 4/1994 |
| JP | 7204209 | 8/1995 |
| JP | 09117456 | 5/1997 |
| JP | 09117457 | 5/1997 |
| JP | 10137258 | 5/1998 |
| JP | 2001029356 | 6/2001 |
| JP | 2002311467 | 10/2002 |
| WO | WO-81/03616 | 12/1981 |
| WO | WO 81/03617 | 12/1981 |
| WO | WO-92/04934 | 4/1992 |
| WO | WO-93/00132 | 1/1993 |
| WO | WO-94/26188 | 11/1994 |
| WO | WO-95/18575 | 7/1995 |
| WO | WO 96/40369 | 12/1996 |
| WO | WO-97/43971 | 11/1997 |
| WO | WO-99/05978 | 2/1999 |
| WO | WO-00/47280 | 8/2000 |
| WO | WO 00/53113 | 9/2000 |
| WO | WO-00/53113 | 9/2000 |
| WO | WO-01/58373 | 8/2001 |
| WO | WO-01/62169 | 8/2001 |
| WO | WO 01/72084 | 9/2001 |
| WO | WO-03/024309 | 3/2003 |
| WO | WO-03/101324 | 11/2003 |
| WO | WO-2004/064606 | 8/2004 |
| WO | WO-2004/071317 | 8/2004 |
| WO | WO-2004/084748 | 10/2004 |

* cited by examiner

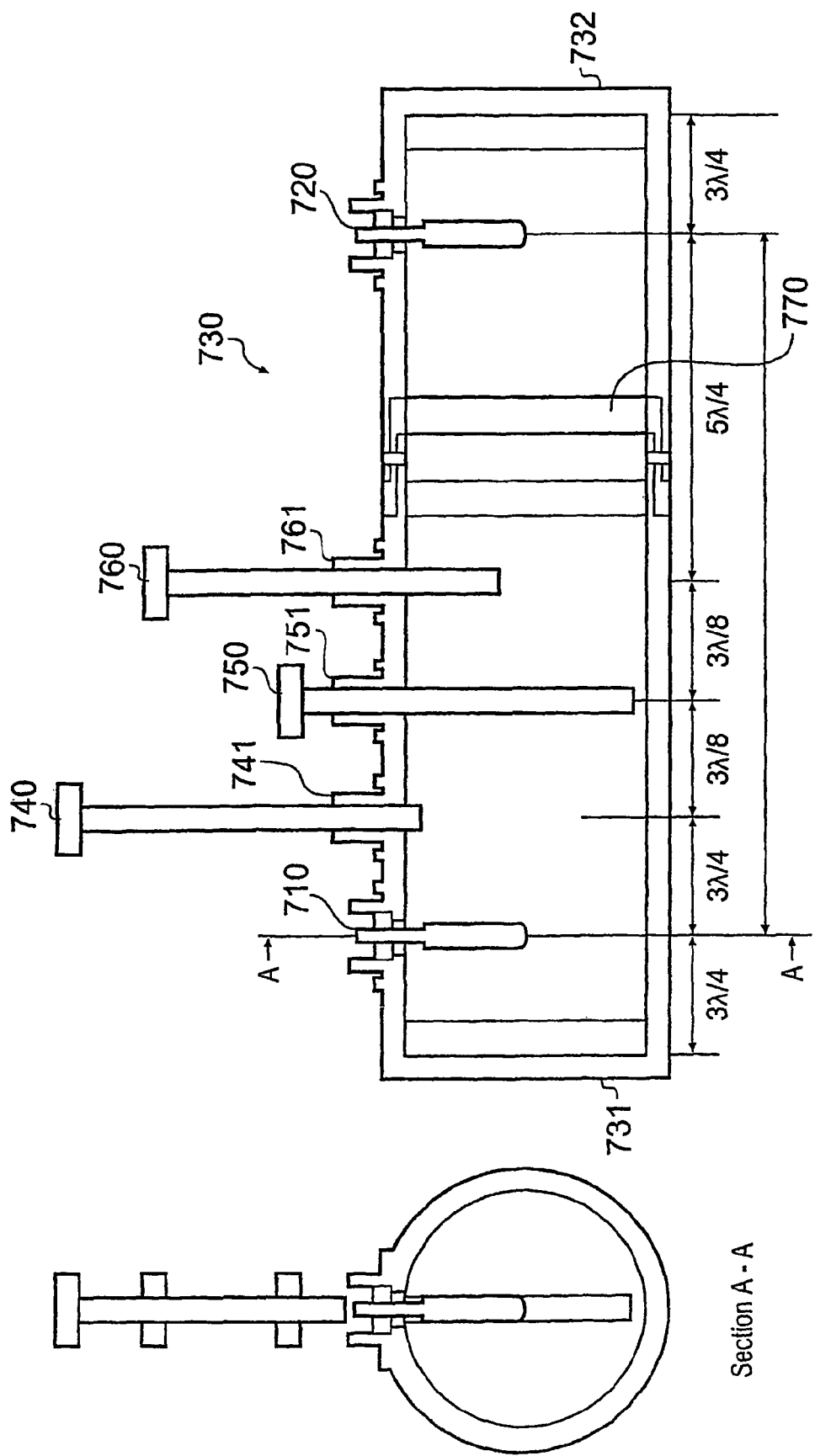

TISSUE ABLATION APPARATUS AND METHOD OF ABLATING TISSUE

BACKGROUND TO THE INVENTION

1. Field of the Invention

The present invention relates to an apparatus and method for ablating tissue with microwave radiation. In this specification microwave means the frequency range from 5 GHz to 60 GHz inclusive. Preferably 14-15 GHz is used for tissue ablation but the present invention is not limited to this narrower range.

2. Summary of the Prior Art

Traditional methods of treating cancer involve removing the cancerous tissue by cutting it out mechanically and/or chemotherapy, usually followed by radiotherapy. Both methods have significant drawbacks and may cause serious trauma to the patient.

The application of heat energy to biological tissue is an effective method of killing cells. Thus the present invention proposes applying microwaves to heat and thus ablate (destroy) biological tissue. This presents an interesting opportunity for the treatment of cancer as the cancerous tissue can be ablated in this way. There is a need for a suitable apparatus and method for ablating tissue with microwaves for the treatment of cancer or other conditions.

SUMMARY OF THE INVENTION

Accordingly a first aspect of the present invention may provide a tissue ablation apparatus comprising:

a source of microwave radiation;

a probe for directing the microwave radiation into the tissue to be ablated;

a local oscillator for producing a signal having a different frequency to said microwave radiation;

a first detector for detecting the magnitude and phase of microwave radiation reflected back through the probe towards the source, said first detector being connected to said local oscillator, and an impedance adjuster having an adjustable complex impedance, between said source and said probe.

In this specification except where the context demands otherwise, the term 'connected' includes not only direct connection but also indirect connection via one or more intermediate components.

The tissue ablation apparatus may comprise:

a source of microwave radiation having a frequency;

a probe connected to said source, said probe being configured for directing said microwave radiation into said tissue to be ablated;

a local oscillator for producing a signal, having a frequency different to said frequency of said microwave radiation;

a first detector for detecting the magnitude and phase of a reflected portion of said microwave radiation reflected back through said probe towards said source;

said first detector being configured to determine the magnitude and phase of said reflected portion of said microwave radiation on the basis of said signal produced by said local oscillator and said reflected radiation, and an impedance adjuster having an input connected to said source of microwave radiation and an output connected to said probe, said input and output having respective complex impedances, said complex impedance of said output being adjustable.

As said adjustable complex impedance of the impedance adjuster can be adjusted, the amount of reflected radiation can be minimised, thus improving the efficiency of the energy delivery to the tissue.

In general the level of radiation reflected back through the probe by a load (e.g. tissue) at the distal end of the probe will be minimised if the impedance at the output of the impedance adjuster is matched with the impedance of the load (e.g. the tissue being ablated).

A channelling means such as a coaxial cable or a waveguide may be used to connect the impedance adjuster to the probe. If the distance travelled by the microwave radiation between the output of the impedance adjustor and the distal end of the probe is equal to a multiple of $\lambda/2$ (where $\lambda$ is the wavelength of the radiation), then it is a simple matter of matching the output impedance of the impedance adjustor to the impedance of the load (e.g. tissue) at the distal end of the probe. Otherwise the impedance can still be matched to minimise reflections, but the impedances of the probe and the channelling means also need to be taken into account (so e.g. the output impedance of the impedance adjustor needs to be matched to the combined impedance of the load, the channelling means and the probe). Therefore it is preferable, but not essential for said channelling means to have an adjustable length whereby the combined length of said channelling means and said probe can be adjusted to be equal to a multiple of $\lambda/2$.

If the detector only provided magnitude (i.e. amplitude or power) information then it would not be possible to adjust the complex impedance quickly enough to effectively minimise the reflected radiation. Another advantage of using phase information is that phase differences can be measured even when the signal to noise ratio is poor. Therefore the detector has to provide both magnitude and phase information. In order to provide phase information it is necessary to have a local oscillator, providing a signal having a frequency different to the frequency of microwave radiation, so that the phase of the detected microwave radiation can be compared with that of the signal from the local oscillator.

Usually the detector will comprise a mixer for mixing the signal from the local oscillator with the microwave radiation. For example the detector may detect the reflected magnitude and phase by heterodyne detection (mixing of the reflected radiation or a signal derived from it with the signal from the local oscillator). Alternatively the phase can be detected by a phase comparator configured to compare the phase of the reflected microwave radiation with that of the local oscillator signal. The reflected microwave radiation may be passed through one or more frequency transformers before entering the mixer or the phase comparator, this is particularly helpful if a phase comparator is used because phase comparators tend to work more accurately at lower frequencies.

Preferably the apparatus further comprises a second detector for detecting the magnitude and phase of forward directed microwave radiation (radiation directed from said source toward said probe).

As for the first detector above, it is necessary to have a local oscillator so that the phase of the microwave radiation can be determined. Preferably the same local oscillator as for the first detector is used. So, for example if the detectors use mixers, then each detector will have its own mixer and both mixers will be connected to a common local oscillator. In such a case the output from the local oscillator may need to be buffered in order to drive two or more mixers. Alternatively each mixer could be connected to a different local oscillator, but that would make it harder to detect the phases and make the appropriate impedance adjustments, because of differences between the local oscillator signals.

The presence of a second detector for detecting the magnitude and phase of 'forward directed' microwave radiation makes it easier to determine the appropriate impedance adjustment. If there is only one detector then more assumptions need to be made about the characteristics of the apparatus (e.g. the phase change caused by the apparatus between the input to the impedance adjuster and the probe/tissue interface).

Preferably there is also a third detector. The third detector is either configured to detect the magnitude and phase of reflected microwave radiation or it is configured to detect the magnitude and phase of 'forward directed' microwave radiation. The third detector enables the appropriate (complex) impedance adjustment to be determined more accurately. When there is a third detector it is possible to monitor the change in complex impedance due to adjustments of the impedance adjuster itself. It may also be possible to directly determine the phase difference between the input and output of the impedance adjuster which information is useful in determining the appropriate adjustment to be made.

As for the second detector, the third detector needs to be connected to a local oscillator. This may be the same local oscillator as for one or both of the first and second detectors, or a different one. Preferably all the detectors share a common local oscillator, again possibly will buffering.

Where a phase comparator is used, the first, and (if present) second and third detectors can be combined into one unit.

The or each local oscillator may be separate and independent from the source of microwave radiation.

Alternatively the or each local oscillator may produce a signal derived from said source of microwave radiation, but having a different frequency. Typically this is done by a frequency transformer which transforms a signal from said source of microwave radiation down to a lower frequency. This lower frequency 'local oscillator' signal can then be input into a mixer of the detector for mixing the forward directed or reflected microwave radiation or used as a reference signal for a phase comparator. In effect the frequency transformer, connected to the source of microwave radiation acts as the local oscillator.

Another approach is to have a separate local oscillator, but to mix the local oscillator signal with a signal from said source of microwave radiation and to input the result of this mixing to the detector. Typically, a filter will be provided between the mixer and the detector itself (which may itself comprise a mixer as noted above) to filter out any unwanted frequencies.

The impedance adjuster may be operated by a human operator in response to data relating to the detected magnitude and phase displayed on a display. Preferably however, said adjustable complex impedance of the impedance adjuster is adjusted automatically by a controller on the basis of the magnitude and phase of the radiation detected by said detector(s). The controller may for example take the form of an integrated circuit or a computer.

Preferably the controller is configured to adjust said adjustable complex impedance dynamically (in real time) in response to the variation in the magnitude and phase of the radiation detected by said detector(s). In this way the impedance can be adjusted as the characteristics of the tissue change during the ablation process. For effective dynamic control the adjustment time would be less than the relaxation time (or response time) of the tissue.

The impedance adjuster may take any suitable form. For example it could be a semiconductor device or a stub tuner. In the case of a stub tuner, the tuner may have one, two, three or more stubs. A three-stub tuner is preferred as this can adopt a wide range of complex impedances (in theory any impedance on the Smith chart). Another possibility is to have an impedance adjuster comprising a phase adjuster and a magnitude adjuster (e.g. two variable length lines or a variable length line and a tuning stub; the variable length line(s) may be coaxial or striplines).

There may be provided electrically activateable actuators for controlling the impedance adjuster. If a stub tuner is used as the impedance adjuster then the electrically activateable actuator(s) may, for example, be one or more piezoelectric devices or servo-motors for controlling the stub(s) to adjust the impedance. The actuator(s) may be controlled by said controller, so that the control of the impedance matching is automatic.

Preferably the source of microwave radiation is a stable single frequency source, for example a phase locked source or a broadband source with a narrow band filter. This is helpful when detecting phase changes, e.g. in the reflected microwave radiation. The source may be a VCO (Voltage Controlled Oscillator) or a DRO (Dielectric Resonator Oscillator); other possible sources will be apparent to a person skilled in the art. The source may be tuneable so that the frequency can be varied in a controlled manner.

The probe can be coaxial or a waveguide (which may be loaded or unloaded).

Preferably the probe is configured to penetrate biological tissue. For example it may have a pointed end. This enables the probe to be inserted into the tissue until it is close to or inside a tumour, which is to be ablated. The microwaves can then be effectively directed at the tumour. It is particularly advantageous to have a probe that is capable of being inserted by key-hole surgery. Accordingly the probe preferably has an outer diameter of less than 1 mm. This small size minimises trauma to the patient and also increases the energy density of the microwave radiation exiting the probe.

The probe may be a coaxial probe—having a central conductor, an outer conductor and a dielectric between said two conductors. There may also be one or more baluns (balanced to unbalanced transformers) on the outer conductor to minimise the return current on the outer conductor (which current may cause shock to the patient or the person operating the apparatus). The baluns may take the form of a ring or sheath of conducting material surrounding the outer conductor. Dielectric baluns can also be used.

Preferably the apparatus has a separator for separating the reflected microwave radiation from the 'incident' (forward directed) microwave radiation being directed out of the probe. This separator may for example take the form of a circulator. Alternatively it could be a power 3 dB coupler.

Preferably the apparatus has a first coupler for directing some of the reflected radiation to the first detector. Any suitable coupler may be used, e.g. a single port coupler, however a six port coupler may be advantageous. There may also be a second coupler for directing some of the outgoing (forward directed) radiation to a second detector. There may be a third coupler for directing radiation to a third detector; said third coupler will either be a reflected radiation coupler or a forward directed radiation coupler. Preferably said couplers are highly directional to ensure good differentiation between forward and reflected radiation.

At its most general a method according to the present invention comprises the step of placing a probe in contact with biological tissue and delivering microwave radiation through said probe to said tissue to ablate at least a portion of said tissue. Preferably the method is used to treat cancer. The tissue may have a cancerous portion, or tumour, in which case the radiation is used to ablate said cancerous portion or tumour, preferably leaving the surrounding non-cancerous tissue substantially unharmed.

Very fine (diameter less than 1 mm) probes will be advantageous in some procedures, but the present invention us not limited to these.

It is thought that the present invention will be especially useful in treating breast cancer. Treatment of brain tumours is another possible application. However the present invention is not limited to these applications. It may also be used to treat lung cancer, liver cancer (e.g. liver metastases), prostate cancer, skin cancer, colo-rectal carcinoma, or any carcinoma where solid tumours are present and can be ablated. Other applications will be apparent to a person skilled in the art. In some embodiments the present invention may be useful for treating conditions other than cancer, for example skin disease or brain disease (especially, but not exclusively in regions near the optic nerve).

Thus, a second aspect of the present invention may provide a method of ablating tissue comprising the steps of:

using a source of microwave radiation to provide microwave radiation;

placing a probe in contact with or inserting a probe into biological tissue;

directing said microwave radiation through said probe into the tissue to ablate the tissue;

detecting the magnitude and phase of microwave radiation reflected back through the probe by using a first detector and a local oscillator, and adjusting the complex impedance of an impedance adjustor between said source and said probe on the basis of the magnitude and phase of the microwave radiation detected by said first detector.

The method may comprise the steps of:

using a source of microwave radiation to provide microwave radiation having a frequency;

placing a probe in contact with or inserting a probe into biological tissue;

directing said microwave radiation from said source through an impedance adjuster and then through said probe into said tissue to ablate the tissue; said impedance adjustor having an input connected to said source and an output connected to said probe, said input and said output having respective complex impedances;

detecting the magnitude and phase of reflected microwave radiation reflected back through the probe by using a first detector and a local oscillator; said local oscillator generating a signal having a frequency different to said frequency of said microwave radiation, said first detector using said local oscillator signal in combination with the reflected radiation or a signal derived from said reflected radiation to determine the magnitude and phase of said reflected radiation;

and adjusting said complex impedance of said output of said impedance adjustor on the basis of said magnitude and phase of said reflected microwave radiation detected by said first detector, so as to minimise the amount of microwave radiation which is reflected back through said probe.

Preferably this method is a method of treating cancer using the apparatus of the first aspect of the present invention.

Preferably the probe is inserted into the tissue until an end of the probe is proximate to or preferably inside a cancerous tumour in the tissue and microwave radiation is then passed through the probe to ablate said cancerous tumour.

Preferably microwave radiation from the probe is used to cut a path in the tissue so that the probe can be inserted near to or into the tumour. This is an effective method of getting the probe close to or into the tumour.

Preferably the microwave radiation from the probe is used to seal the path of the probe on exiting the tissue and/or the body being treated.

Preferably the magnitude and phase of forward directed microwave radiation directed into said probe from said source of microwave radiation is detected by a second detector and a local oscillator and said adjustable complex impedance of said impedance adjuster is adjusted based on the magnitudes and phases detected by said first and second detectors, e.g. on the basis of the phase and magnitude difference between the forward directed and reflected radiation.

Preferably a third detector is used to detect the magnitude and phase of either forward directed or reflected radiation and said adjustable complex impedance of said impedance adjustor is adjusted on the basis of information provided by said first, second and third detectors, e.g. on the basis of the magnitude and phase differences between the detectors.

Preferably said adjustable complex impedance of the impedance adjuster is adjusted automatically by a controller on the basis of the magnitude and phase detected by said detectors so as to minimise the amount of radiation reflected back through said probe.

Preferably the impedance adjustment is carried out dynamically (in real time) as the detected magnitude and phase varies. This enables said adjustable complex impedance of the impedance adjuster to be adjusted as the impedance of the tissue changes during the ablation process. This minimises probe and cable heating (caused by reflected energy in the apparatus for long period of time), and may help to provide a fast, efficient controlled ablation process.

Further preferred features may be found in the claims.

A third aspect of the present invention provides an elongate microwave probe for delivering microwave radiation into tissue to be ablated, said probe having an elongate portion and a tip at one end of said elongate portion, said tip being formed of a ceramic material and being configured to deliver microwave radiation into tissue.

Ceramic material is suitable for the tip; because ceramics are relatively hard, can have a high permittivity ($\in_r$) which helps to focus EM fields and a good thermal conductivity which reduces heating of the tip.

Preferably the tip is cone or dome shaped. This helps to focus microwaves leaving the probe.

Preferably the ceramic is a microwave ceramic. For example microwave ceramics from Pacific Ceramics Inc., could be used.

Preferably the microwave ceramic has a permittivity greater than unity, more preferably from $\in_r$=6.5 to $\in_r$=270 at microwave frequencies. Preferably the microwave ceramic has low loss (tan δ) at the microwave frequencies of interest.

A fourth aspect of the present invention provides a coaxial tissue ablation probe having an inner conductor, a dielectric surrounding said inner conductor, a conducting sheath surrounding said dielectric and one or more baluns on said sheath, the or each balun comprising a spray-on dielectric. Preferably the or each balun also comprises an outer conductor surrounding said spray-on dielectric. As the dielectric is a spray-on dielectric it is possible to make the baluns very small. This is necessary where the probe is of small cross-section and/or the frequencies high.

According to a fifth aspect of the present invention there is provided a method of making a balun for a coaxial tissue ablation probe comprising the steps of spraying or otherwise placing a liquid or powder dielectric onto an outer surface of an outer conducting sheath of a coaxial probe, if said dielectric is liquid allowing the liquid to solidify, to form the balun.

In both the fourth and fifth aspects of the present invention, preferably said probe is designed for use with a microwave radiation of wavelength λ and the balun has a length in the direction of the axis of said probe approximately equal to λ/4 or add multiples thereof.

A sixth aspect of the present invention provides a surgical apparatus comprising:

a source of microwave radiation of a first frequency suitable for ablating tissue;

a probe for directing microwave radiation from the source into tissue to be ablated;

a modulator having an OFF state in which it does not modulate said microwave radiation from the source and an ON state in which it modulates microwave radiation from the source in pulses having a second frequency less than said first frequency; said second frequency being suitable for cutting tissue. Thus the probe can output two different frequencies—one optimised for tissue ablation (e.g. for ablating cancerous tissue), the other for tissue cutting (e.g. through healthy tissue to get to the cancerous tissue)—but the apparatus only needs one source of radiation. This is better than having two separate radiation sources.

Preferably the first frequency, for tissue ablation, is 1 GHz or higher, more preferably 13 GHz or higher. In one embodiment it is in the range 14-15 GHz.

The second frequency, for tissue cutting, is preferably in the range of 10 kHz to 500 MHz. These frequencies have been found to be efficient at tissue cutting. More preferably the range to 500 kHz to 30 MHz.

Preferably the apparatus further comprises a low pass filter between said modulator and said probe; said low pass filter having a first state in which it lets said first frequency pass and a second state in which it passes said second frequency, but filters out said first frequency. The apparatus works without the filter, but the filter improves the cutting effect of the second frequency.

Preferably said modulator is capable of varying said second frequency.

Preferably said low pass filter is capable of varying its pass band in its second state when the modulator frequency is varied. This makes the apparatus more flexible.

Any of the features of the first to sixth aspects of the present invention described above may be combined with each other.

BRIEF DESCRIPTION OF THE DRAWINGS

Embodiments of the present invention will now be described with reference to the accompanying drawings in which:

FIG. 7 shows an impedance adjuster;

FIG. 8 is a cross sectional view of the impedance adjuster of FIG. 7 along the line A-A of FIG. 7;

DETAILED DESCRIPTION OF THE INVENTION

Overview of the Apparatus

Figure 1:
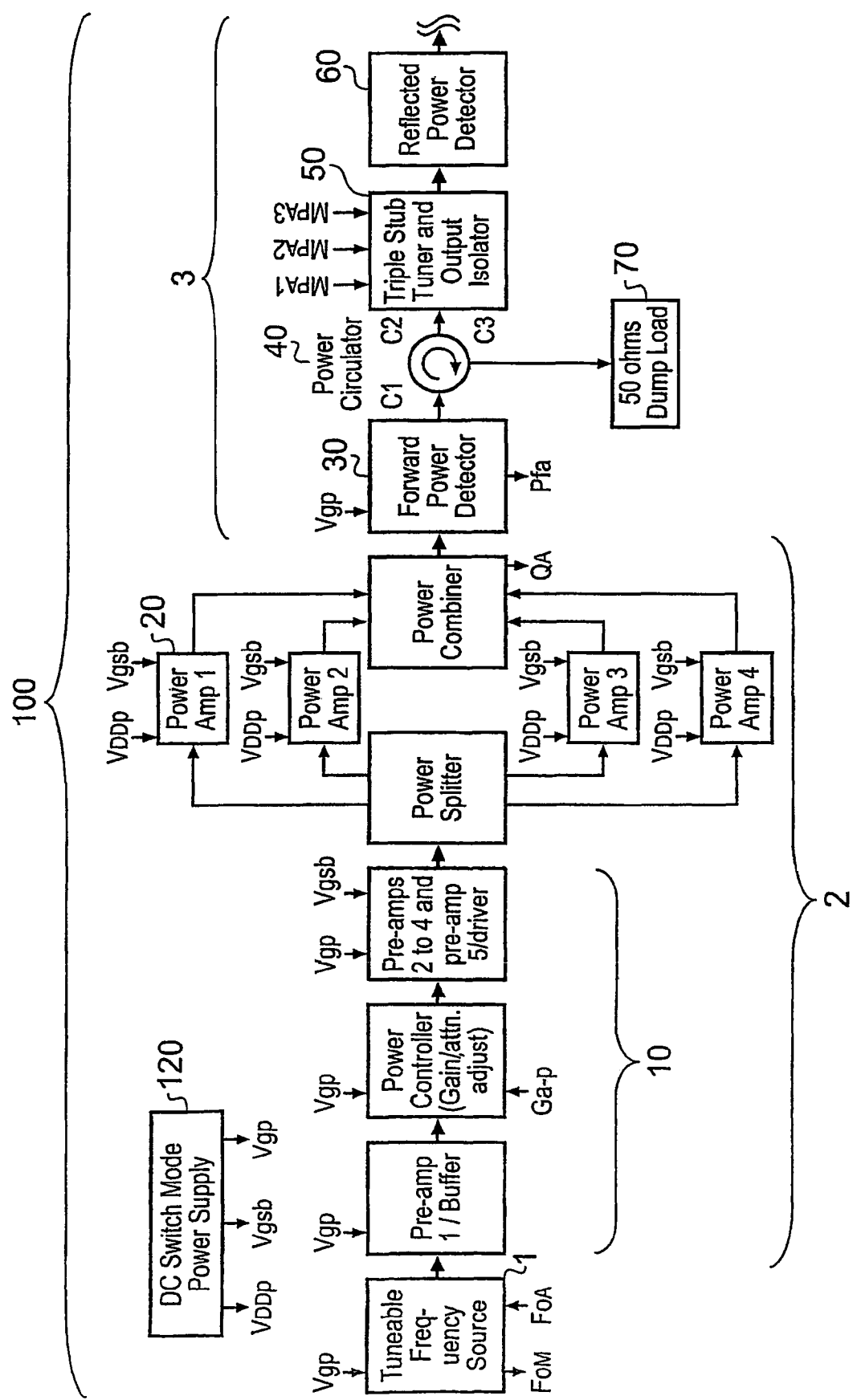
FIG. 1 is a block diagram of a tissue ablation apparatus that uses microwaves.
Figure 1:
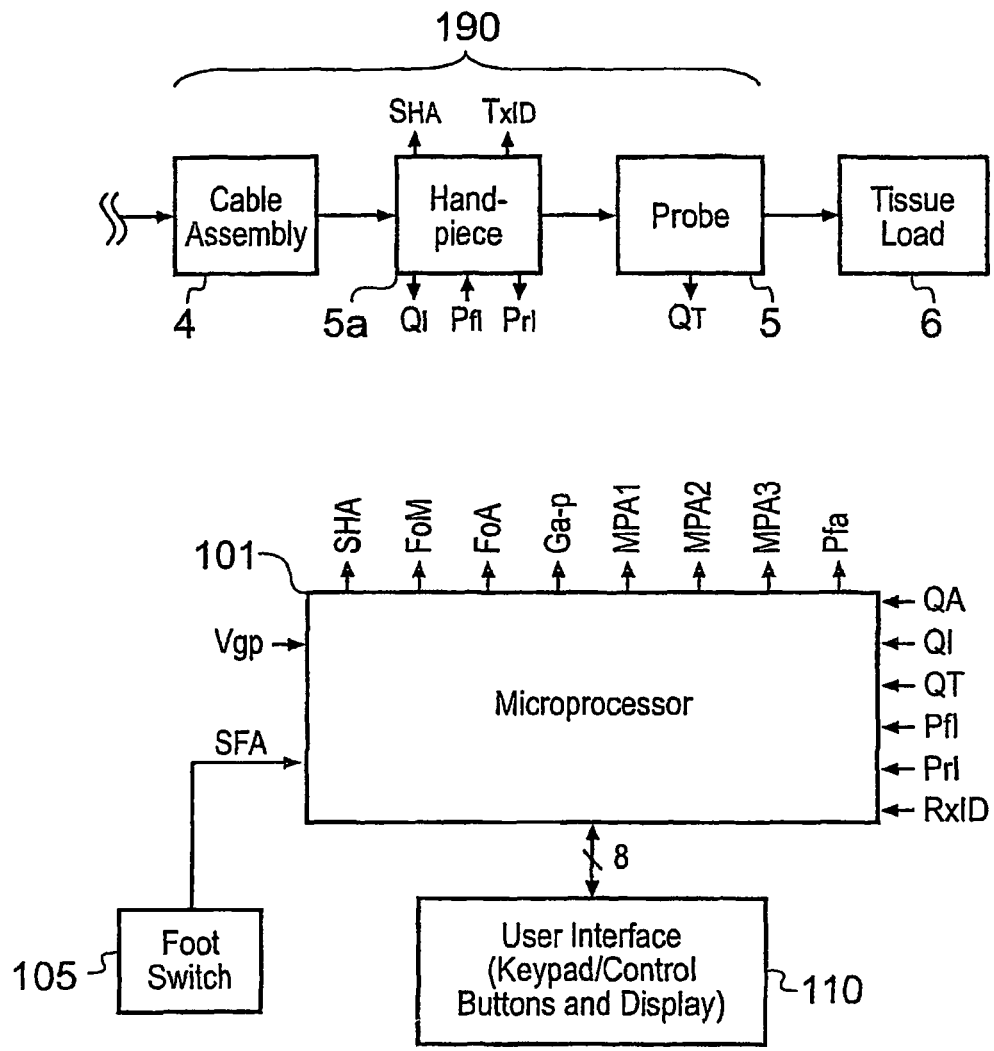

A block diagram of an apparatus for ablating tissue with microwaves is shown in FIG. 1. The apparatus has a unit 100 for generating and controlling the microwave radiation and grouped generally under reference numeral 190 a probe 5 and a channelling means 4 for delivering the microwave radiation to the probe. The probe 5 can be used to apply the microwave radiation to tissue 6 in order to ablate the tissue.

As the tissue 6 may reflect some of the microwaves back into the probe 5 and the unit 100, it is necessary to have a way of impedance matching the apparatus 100, 200 to the tissue 6. This is provided by components generally grouped under reference number 3 for monitoring the reflected microwaves and adjusting the impedance accordingly. This important part 3 of the apparatus takes into account both the magnitude and phase of the reflected microwaves. In the present embodiment it is provided as a sub-unit in the unit 100. It is described in more detail later.

The unit 100 comprises a source of microwave radiation 1, an amplifying system 2 for amplifying microwaves from the source 1, components 3 for detecting microwaves and adjusting impedance, a power supply 120 and a controller 101 for controlling the amplifying system 2 and the unit 3 accordingly.

The unit 100 is connected to the probe 5 by channelling means 4 and a holder 5*a*. The channelling means 4 may take any form suitable for channelling microwaves, for example a waveguide or a coaxial cable. It is advantageous if the channelling means 4 and the probe have a combined length equal to a multiple of λ/2 (where λ is the wavelength of the microwave radiation generated by the source 1), because this makes the channelling means 4 and the probes transparent to the microwave radiation, so that their impedances can be ignored when impedance matching the tissue 6 to the apparatus 100, 200. This makes impedance matching easier. Accordingly there may be length adjuster so that the effective length of the channelling means can be adjusted. Possible length adjusters include a telescopic connector, a coaxial trombone phase adjuster or a pin diode phase adjuster. The impedance matching is discussed in more detail later.

The microwave amplifying system 2 has a pre-amplifier 10 and a power amplifier 20, both of which are described in more detail later.

The unit 3 has a first detector 60 for detecting the magnitude and phase of microwaves reflected back into the apparatus (reflected microwave radiation) and a second detector 30 for detecting the magnitude and phase of the microwaves being directed towards and through the probe 5 ('forward directed microwave radiation'). These two types of microwave radiation are discriminated by their direction and so the detectors may be termed forward 30 and reverse (or reflected radiation) 60 detectors respectively.

The unit 3 has a circulator 40 for separating microwaves travelling to the probe from microwaves reflected back into the probe (e.g. microwaves reflected by the tissue 6). While the detectors are preferably designed to be capable of discriminating the forward and reflected microwaves, it is highly preferable to have a circulator 40 as well for the following reason. The circulator 40 acts as an isolator for preventing reflected radiation being directed back into the amplifying system 2, which could damage the amplifiers.

The circulator 40 has three ports C1, C2 and C3 connecting it to the surrounding circuitry. Port C1 connects it to the source 1 via the forward detector 30 and the amplifying system 2, port C2 connects it to the probe via the impedance adjuster 50, the reverse detector 60 and the channelling means 4, and port C3 connects it to a dump load 70. Radiation entering at C1 exits the circulator at C2 and reflected radiation entering the circulator at C2 exits the circulator at C3. A power yttrium iron garnet (YIG) circulator may be used.

Detectors

Figure 2:
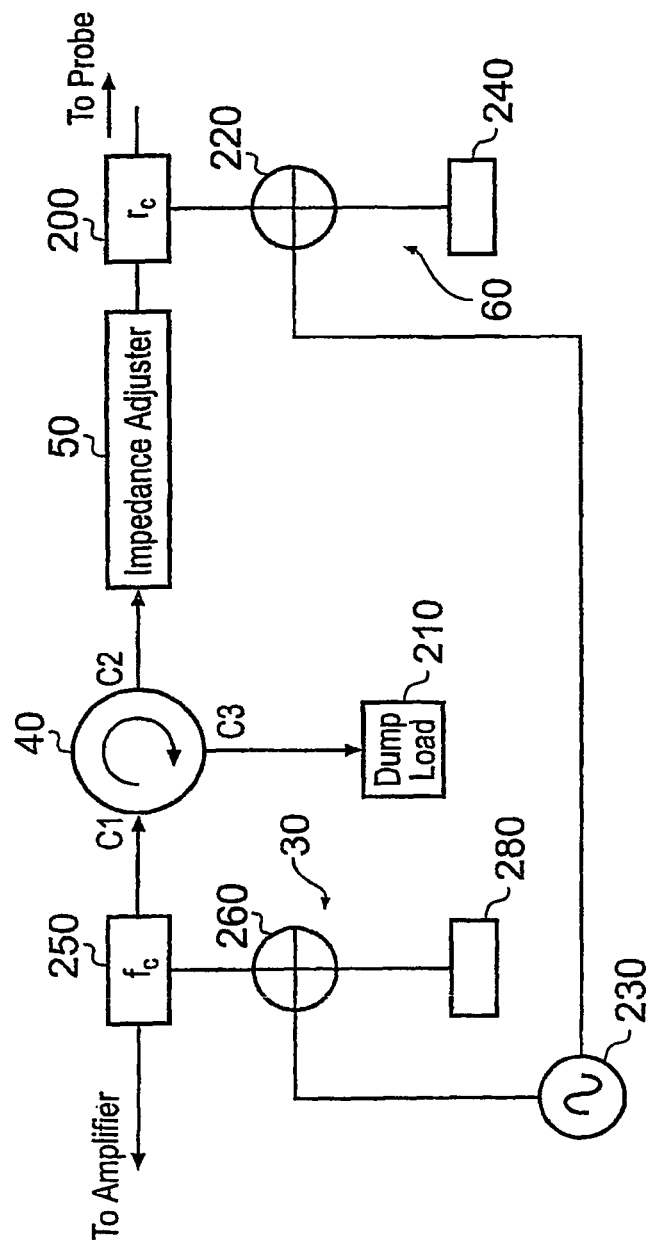
FIG. 2 is a schematic diagram showing the forward power detector, reflected power detector and circulator of the apparatus of FIG. 1 in more detail.

As mentioned above the detectors 30, 60 detect both the magnitude and phase of the microwave radiation. FIG. 2 is a schematic diagram showing the unit 3 and in particular the detectors 30, 60 in more detail. The first power detector 60 for detecting the magnitude and phase of microwave radiation reflected back through the probe comprises a directional coupler 200 connected to the impedance adjuster 50 which is connected to port C2 of the circulator. The directional coupler 200 directs a portion of the reflected radiation to mixer 220 where it is mixed with a signal from a local oscillator 230.

This mixing produces an intermediate frequency signal that is detected by detecting device 240, connected to an output of said mixer 220, so that both the magnitude and phase of the reflected radiation can be derived. In other words the system is a heterodyne detection system. There may be a filter (not shown) between the detecting device 240 and the mixer 220 to filter out unwanted frequencies produced by mixing. The magnitude and phase information is sent to the controller 101. In alternative embodiments the function of the device 240 may be carried out by the controller itself. In such a system, it is preferable that the intermediate frequency is generated on the difference between the frequency of the signal from the local oscillator and the frequency of the reflected radiation. However, it is also possible for the intermediate frequency to be the source of the frequency of the signal from the local oscillator and the frequency of the reflected radiation.

It is necessary to have the local oscillator 230 so that the phase as well as the magnitude can be detected. In other embodiments the reflected radiation may be passed through frequency transformers and/or other devices between the directional coupler 200 and the mixer 220 to make it easier to handle before it is mixed with the signal from the local oscillator.

The second detector 30 comprises a directional coupler 250 which couples the majority of incoming radiation to port C1 of the power circulator 40, but directs a portion to a second mixer 260 connected to said local oscillator 230 and a detecting device 280 arranged in the same manner as described above for the first detector 60.

In an alternative embodiment it would be possible for the first and second detector 30, 60 to be connected to different local oscillators, rather than one common oscillator 230 as shown in FIG. 2.

It will be appreciated to those skilled in the art that the components need not be in the order shown in FIGS. 1 and 2. For example the detectors and impedance adjuster 3 could be at the end of the channelling means 4 between the channelling means 4 and the probe 5. It would also be possible to separate the components and/or rearrange their order. For example, the forward coupler 250 could be placed between the circulator 40 and the impedance adjuster 50 or even between the circulator 40 and the dump load 210. It would also be possible to have an apparatus with only the first detector 60 for detecting reflected radiation, although more information is provided if there are both forward and reverse detectors and this makes it easier to work out the appropriate impedance adjustment to the impedance adjustor to minimise the amount reflected radiation.

Figure 17:
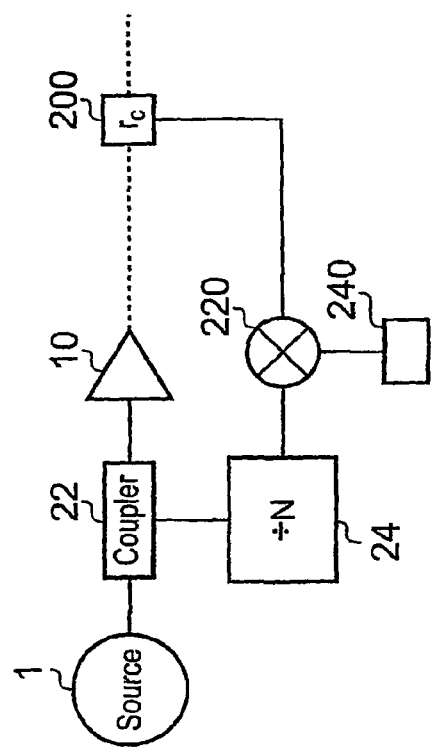
FIG. 17 shows a configuration in which the local oscillator signal is derived from the signal provided by the source of microwave radiation.
Figure 18:
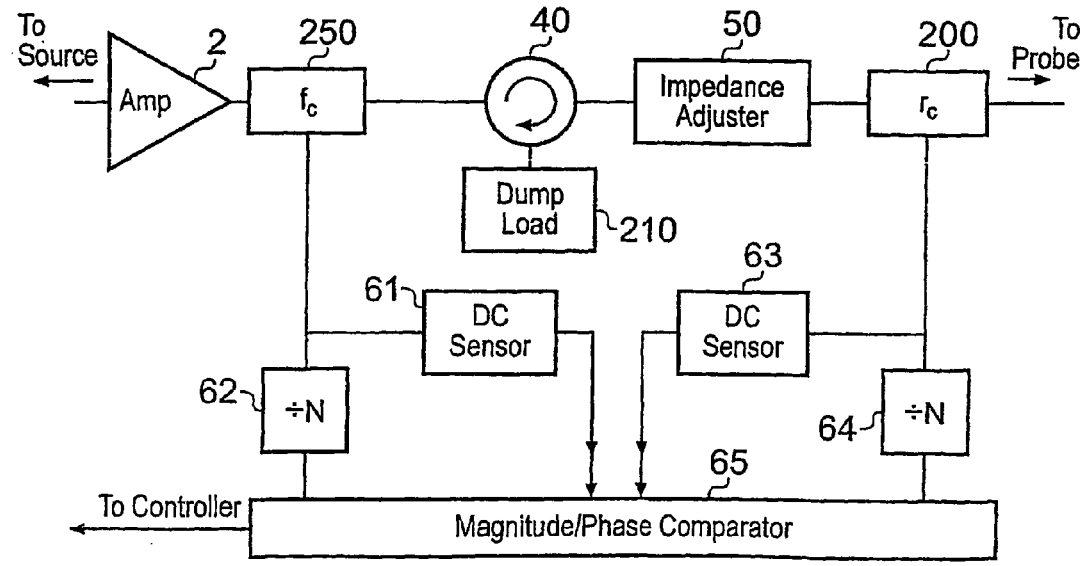
FIG. 18 shows an alternative detection arrangement using a phase comparator.

FIG. 18 shows an alternative arrangement to that of FIG. 2 in which there are no mixers, but a phase comparator 65 is used instead. Like reference numerals indicate like parts as in FIGS. 1 and 2. There is a forward coupler 250, a circulator 40, and impedance adjuster 50 and a reverse coupler 200 as described for FIG. 2. However forward directed microwave radiation from the forward coupler 250 is sent first to an frequency transformer 62 which acts as a local oscillator as in the arrangement of FIG. 17 and a magnitude sensor (in this case a DC sensor) 61 and then from each of these to the phase comparator 65. The frequency transformer 62 transforms the microwave radiation to a lower frequency which can be handled by the phase comparator 65. The reverse coupler 200 is connected to a magnitude sensor 63 and a frequency transformer 63, which are each connected to the phase comparator in the same fashion for the corresponding parts 61 and 62 for the forward coupler 250. The phase comparator 65 takes the magnitude (power) information input from the magnitude sensor 61 and 63 and the transformed frequency signal from the frequency transformers 62 and 64 and from this works out the magnitudes and phases of the forward and reverse directed microwave radiation and sends this information to the controller 101.

It is important that the local oscillator 230 provides a signal having a different frequency to the frequency of the microwave radiation provided by the source 1. This is important in the FIG. 2 configuration, where mixers are used, because two different frequencies are needed for heterodyne detection. It is also important in the FIG. 18 configuration in which the frequency transformer 62 acts as a local oscillator because phase comparators are only able to handle satisfactorily frequencies much lower than the microwave frequencies produced by the source 1.

In the FIG. 2 example the local oscillator 230 is separate and independent from the source 1. However, it would be possible for the local oscillator to provide a signal derived from the source of microwave radiation 1. For example, as shown in FIG. 17, a coupler 22 could be provided between the source of microwave radiation 1 and the pre-amplifying system 10 and configured to divert a portion of the microwave radiation to a frequency transformer 24. The frequency transformer 24, in effect acts as the local oscillator. It is connected to a mixer 220 and output a signal having a frequency different (usually much lower) from the frequency of the microwave radiation from the source 1 to the mixer 220. A reverse coupler 200 directs reflected microwave radiation to the mixer 220. The magnitude and phase of the reflected microwave radiation are determined by detecting device 240 connected to an output of the mixer 220. The other parts of the apparatus are not shown in FIG. 17 and would be the same as described previously in FIGS. 1 and 2.

Figure 16:
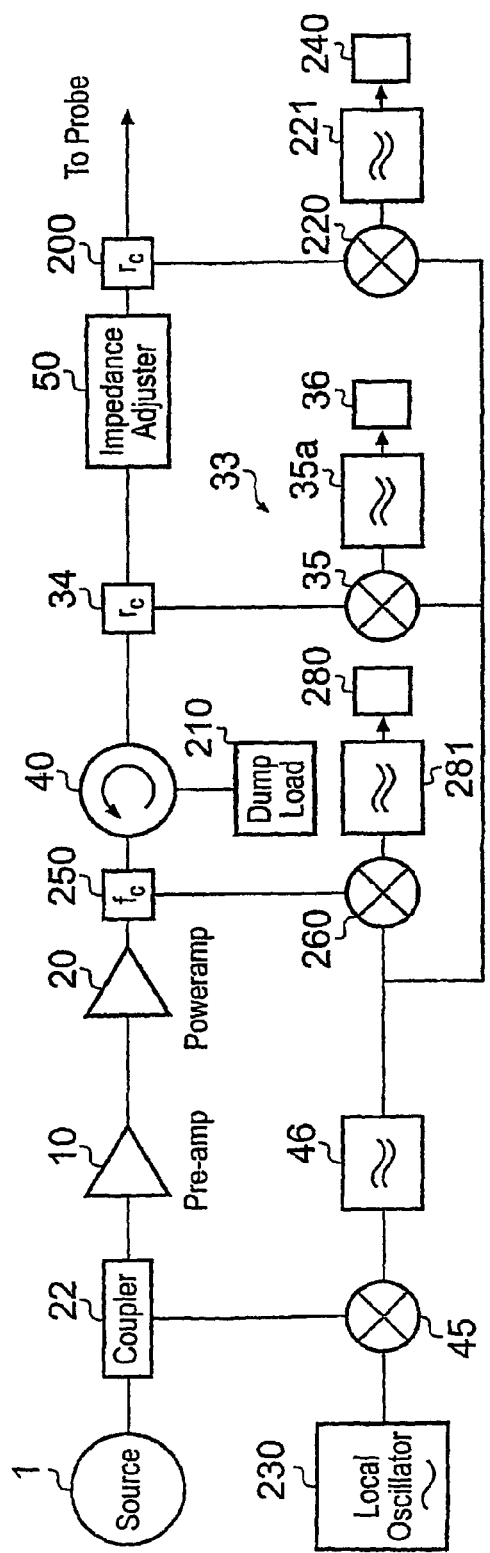
FIG. 16 shows an alternative embodiment of the apparatus in which a signal from a local oscillator is combined with a signal from the source of microwave radiation.

FIG. 16 shows an alternative embodiment of the apparatus in which like reference numerals indicate like parts to those described previously. There are two main differences. The first is that there is an additional detector indicated generally by reference numeral 33, positioned between the circulator 40 and the impedance adjuster 50. As will be appreciated by a person skilled in the art it could be positioned elsewhere e.g. between the circulator 40 and the dump load 210 or between the circulator 40 and the source 1. In the FIG. 16 embodiment the third detector 33 is configured to detect reflected microwave radiation, although in alternative embodiments it could be configured to detect forward directed microwave radiation. It comprises a reverse coupler 34, which is positioned between the circulator 40 and the impedance adjuster 50, a mixer 35 connected to the reverse coupler 34 and a detecting device 36. The third detector 33 operates in the same fashion as the first and second detectors described previously. It provides further information which is helpful in determining the appropriate impedance adjustment to be made by the impedance adjuster 50 so as to minimise the amount of reflected microwave radiation.

The second main difference in the FIG. 16 embodiment is that a signal from the local oscillator 230 is mixed with a signal from the source of microwave radiation 1 in a mixer 45. It is the output signal from the mixer 45, rather than the signal directly from the local oscillator 230, which is input to the first, second and third detectors. The output of the mixer 45 is connected to a filter 46 which removes unwanted frequencies (usually the lower frequencies) produced in the mixer and passes the desired frequency to the inputs of the mixers 220, 260 and 35 of the first, second and third detectors. FIG. 16 also shows respective filters 221, 281 and 35a between the respective detectors' mixers 220, 260 and 35 and their respective detecting devices 240, 280 and 36.

The advantage of having a local oscillator signal which is derived from the source of microwave radiation (as in FIG. 17) or mixed with a signal from the source of microwave radiation (as in FIG. 16) is that the signal sent to the detectors then reflects any change in the frequency or phase of the source of microwave radiation.

Impedance Adjuster and Controller

The impedance adjuster in this embodiment takes the form of a triple stub tuner 50, which is described in more detail later. In other embodiments a single, or double stub tuner or a semiconductor device for adjusting impedance could be used instead.

The impedance adjuster 50 is controlled by a controller 101 on the basis of the magnitude and phase detected by the detectors so as to minimise the amount of reflected microwave radiation. In this embodiment the controller 101 is an integrated circuit; in other embodiments it could be a computer with appropriate software.

The impedance adjustor 50 has an input connected, via the other components shown in FIGS. 1 and 16, to the source of microwave radiation 1 and an output connected via one or more other components, to the probe 5. Usually the source of microwave radiation 1 will have a fixed real impedance and this will be matched with the impedance of the input of the impedance adjuster 50. Therefore the impedance of the input of the impedance adjuster 50 will in most cases be fixed. The complex impedance of the output of the impedance adjuster 50 is adjustable. By adjusting the complex impedance of the output of the impedance adjuster 50 it is possible to minimise the amount of radiation which is reflected from the tissue back through the probe 5. If the distance travelled by the microwave radiation between the output of the impedance adjuster 50 and the distal end of the probe 5 is equal to a multiple of the wavelength of the microwave radiation divided by 2, then the complex impedance of the output of the impedance adjuster 50 can be matched directly to that of the tissue 6. If, however, it is not equal to such a multiple then the impedance of the components between the output of the impedance adjuster and the tissue/probe interface need to be taken into account (which is possible but which requires more computation by the controller 101).

There is also provided a user interface 110 allowing the operator to monitor the functioning of the apparatus, in particular the reflected magnitude and phase and optionally also the forward magnitude and phase, measured impedance of the load (tissue 6) to which the probe is applied, and amount of time for which the microwave radiation has been applied.

The user interface 110 also allows the operator to control the apparatus, adjust the power of microwaves by control of the amplifying system 2 through the controller 101 and start and stop the application of microwaves by the controller 101 or the power supply 120. This control may be affected through a foot switch or pedal 105.

Some Possible Applications of the Apparatus

The apparatus may be used to treat cancer by ablating a cancerous tissue. This may be performed by key-hole surgery whereby a small channel is cut into the surrounding tissue through which the probe can be inserted until it reaches the cancerous tumour. The microwaves can then be used to ablate the tumour, the magnitude and phase of reflected microwaves being monitored as described above so that the impedance of the apparatus can be adjusted accordingly to minimise reflection of microwaves back into the probe. The microwaves may be emitted (generated by the source 1) when the probe is proximate the tumour or before. One possible method is to use the microwaves emitted from the probe 5 to cut a path through the surrounding tissue through which the probe can be inserted.

The source 1, amplifying system 2 and probe 5 will now be described in more detail.

Source of Microwave Radiation

In this embodiment the source of microwave radiation 1 is a voltage-controlled oscillator (VCO) whose frequency can be adjusted between 14 GHz and 14.5 GHz. In other embodiments different types of microwave source, e.g. a Dielectric Resonance Oscillator (DRO), or different frequency ranges could be used. VCO control and monitoring signals FoA and FoM are sent to and from the controller 101 (see FIG. 1) respectively.

It is preferred that the source of microwave radiation 1 is capable of outputting power at 0 dBm and that its power level can remain constant with +/−0.5 dB over its output frequency band. The output frequency can be varied within the band (via the controller 101) and this may be used to fine-tune the apparatus. For example there may be a specific frequency within the band whereby circuit resonances occur in the amplifying system 2 and maximum power can be achieved. It is also possible to sweep the frequency over the band to provide some instrument tuning, e.g. increase the frequency where the probe 5 and/or channelling means 4 are slightly too short for resonance or vice versa.

Figure 19:
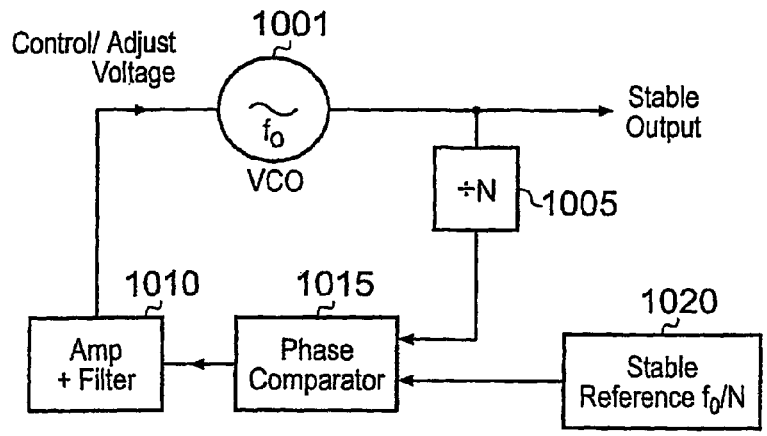
FIG. 19 shows a phase locked source.

It is highly preferable that the source of microwave radiation is stable (i.e. provides a stable output). This assists the phase detection discussed above. One possible way of achieving stability is to use a phase locked source. A possible configuration for a phase locked source of microwave radiation is shown in FIG. 19. A VCO 1001 generates microwave radiation which is output to the rest of the apparatus via an amplifying system 2 as shown above in FIG. 1. A portion of the output signal from the VCO is coupled to a frequency transformer 1005 which reduces the frequency of the signal and inputs it to a first input of a phase comparator 1015. A stable reference signal, such as a signal from a crystal oscillator, is input into a second input of the phase comparator. This is used to track any variation from the desired frequency of the microwave radiation $f_0$. The frequency provided by the stable reference is $f_0/N$ and this can be stable because at lower frequencies very stable oscillators, e.g. crystal oscillators are available. The frequency transformer 1005 reduces the frequency output from the VCO by factor N. The phase comparator 1015 outputs the difference between the frequency and/or phase of the two input signals to an amplifier and filter 1010 which feeds back to the input of the VCO to control and adjust its controlling voltage accordingly to correct any unwanted variation in the frequency and phase of the output signal.

Figure 20:
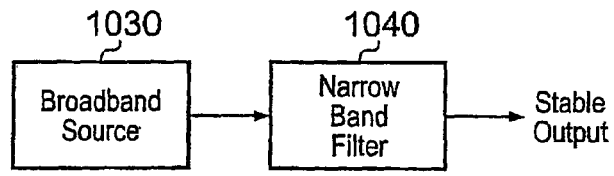
FIG. 20 shows a broadband source combined with a narrow band filter.

FIG. 20 shows an alternative configuration for obtaining a stable output from the source of microwave radiation. A broadband source 1030 (which may be synthesised) is used to provide a wide range of microwave frequencies which are output to a narrow band filter 1040 which select a narrow band of frequencies (or one frequency) to be output. In this way a stable output of microwave radiation can be achieved.

Amplifying System

The amplifying system 2 comprises a pre-amplifier stage or unit 10 and a power amplifier stage or unit 20.

Figure 3:
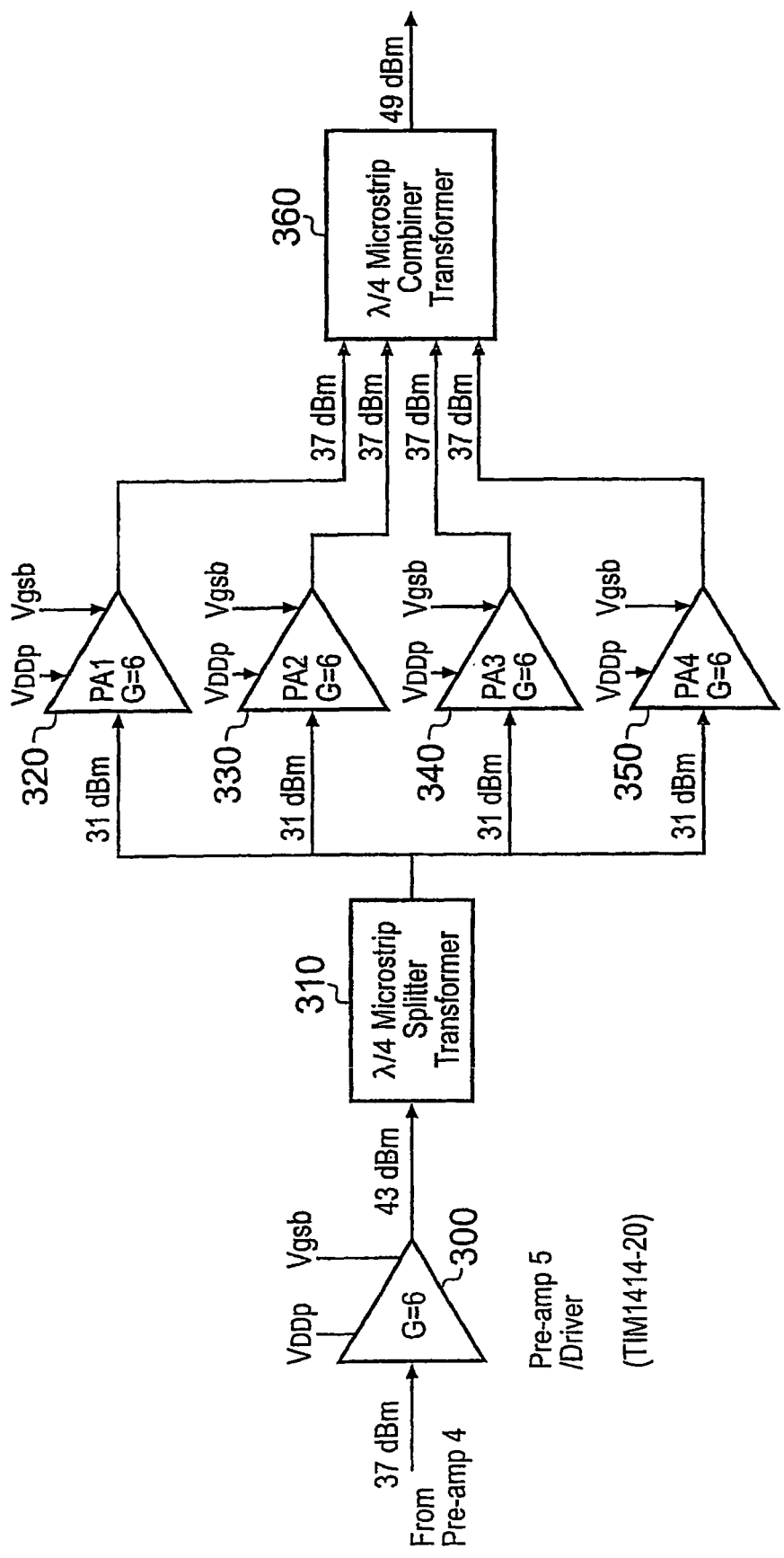
FIG. 3 is a diagram of part of a power amplifier stage in the apparatus of FIG. 1 for amplifying microwaves produced by the microwave source.

One possible configuration of the power amplifier stage 20 is shown in FIG. 3. Microwave radiation is input to a preamp driver 300 from the output of the pre-amplifier stage 10. The preamp driver 300 outputs the radiation to a splitter 310 which divides the signal between four power amplifiers 320, 330, 340 and 350. The signal is amplified and output by each power amplifier and recombined by a combiner 360. Combiner 360 outputs the recombined signal to the detectors and impedance adjuster 3.

The choice of power amplifiers is determined by frequency output by the microwave radiation source 1. For the 14 to 14.5 GHz range, GaAs FETs are particularly suitable. These preferably have a 1 dB compression point of 43 dBm (20 w) over the bandwidth and a power gain of 6 dB. TIM1414-20 from Toshiba Microwave Semiconductor Group may be used. When power amplifiers of this type are used the theoretical maximum output power level is 49 dBm (80 W).

In the FIG. 3 example the splitter 310 and combiner 360 are quarter wavelength microstrip devices.

Alternatively the amplifying system may have one or more microwave couplers for splitting the input signal between a plurality of power amplifiers and one or more microwave couplers for recombining the signals output from said power amplifiers. This has the advantage that if one of the power amplifiers fails then the mismatched energy can be diverted to a dump load connected to the isolated port of the coupler to which the failed power amplifier is connected and the other power amplifiers are not affected.

Figure 4:
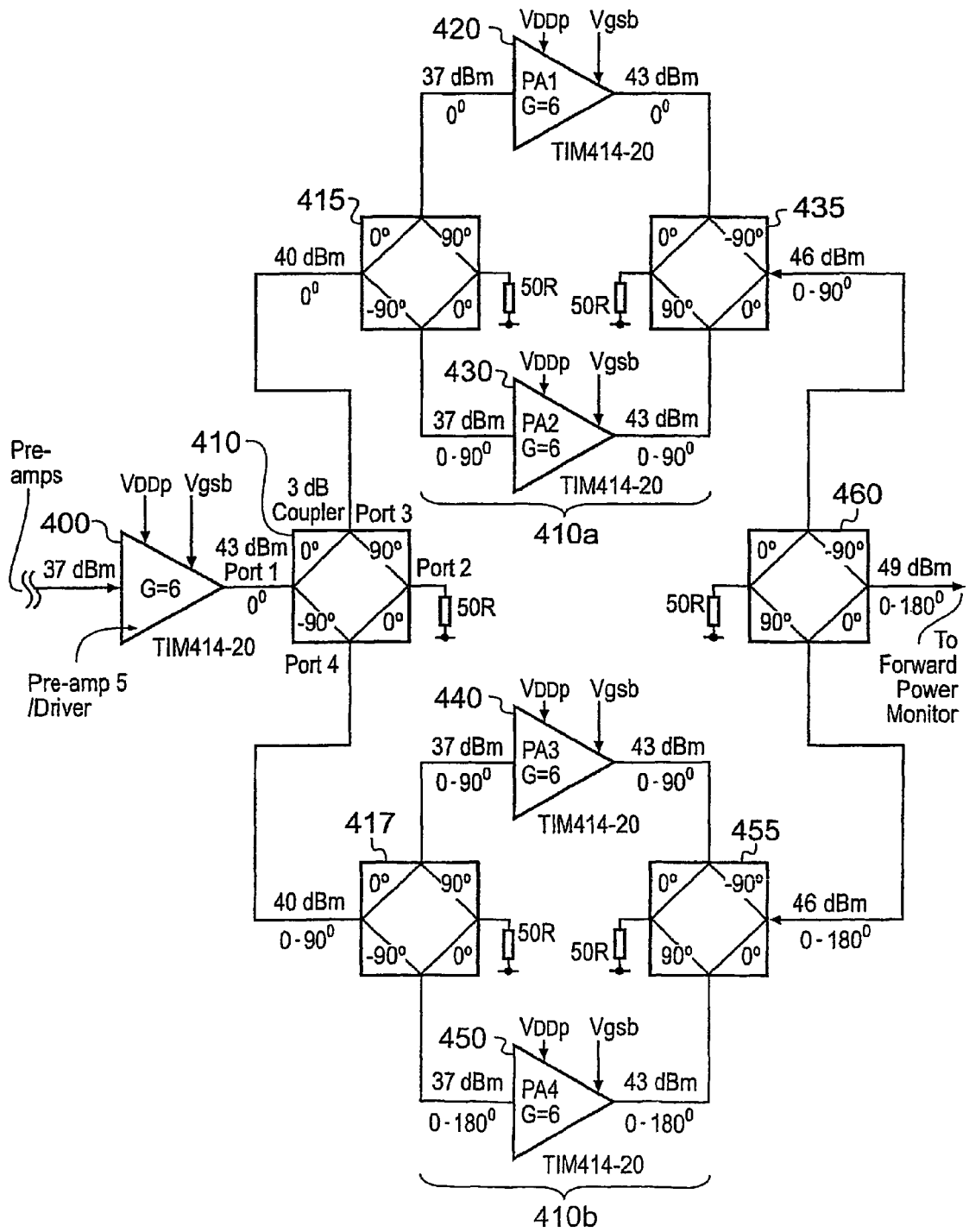
FIG. 4 is a diagram of an alternative power amplifier stage.

FIG. 4 is an example of an arrangement using microwave couplers. A pre-amp driver 400 is used as in the FIG. 3 example, but the arrangement for splitting the signal between the power amplifiers and recombining the amplified signals differs. The signal is split in two stages. The output of the pre-amplifier driver 400 is connected to a coupler that splits the signal between two outputs (ports 3 and 4 in FIG. 4). The signal from the first of these outputs is then directed to a first arm of the circuit 410a where it is split in two again by another coupler 415 which directs the now twice split signal to first and second power amplifiers 420 and 430 and is recombined by a coupler 435. The coupler 435 outputs the signal to the input of a coupler 460.

The signal from the second port of the coupler 410 is directed to a second arm 410b of the circuit which has essentially the same construction as the first arm 410a above. Thus it has a coupler 417 for splitting the signal between a first port and a second port. The first port of said coupler is coupled to the input of a third power amplifier 440 and the second port to a fourth power amplifier 450. The outputs of said third and fourth power amplifiers 440, 450 are coupled to first and second input ports of a further coupler 455 for combining the input signals and the output of said further coupler 455 is connected to the coupler 460 for combining the signals from the two arms 10a, 10b of the circuit.

Although TM414-20 amplifiers are used as power amplifiers in FIG. 4, any suitable power amplifier can be used with appropriate modifications. Mitsubishi MEFK44 A4045 amplifiers may be advantageous.

The couplers 410, 415, 435, 417, 455 and 460 preferably split the power equally between their two outputs or combine equally from their two inputs, such couplers are known as 3 dB 90° couplers.

As explained above, the advantage of the configuration of FIG. 4 is that if one of the power amplifiers fails then the mismatched energy is diverted to a dump load connected to the isolated port of the coupler to which the failed power amplifier is connected. Thus the other power amplifiers are not affected.

Other configurations for the power amplifier stage will be apparent to a person skilled in the art.

The amplifying system 2 has a power level controller. The power level controller is controlled by the controller 101 to give the desired level of output power. In the present embodiment the power level controller is in the pre-amplifying stage 10 of the amplifying system 2.

Figure 5:
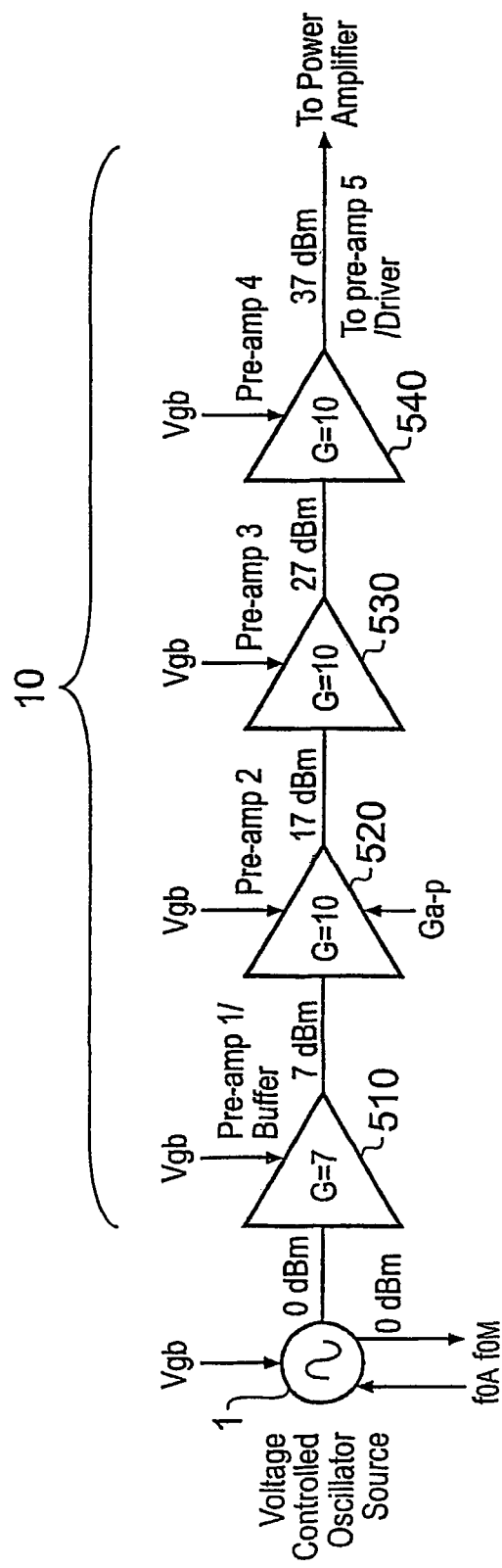
FIG. 5 is a diagram showing the source of microwave radiation and a pre-amplifier stage in the apparatus of FIG. 1.

An example of one possible configuration for the pre-amplifier stage 10 is shown in FIG. 5. The output of the source of microwave radiation 1 is connected to the input of the pre-amplifier stage 10. The pre-amplifier stage 10 comprises a plurality of pre-amps 510, 520, 530 and 540, which in the FIG. 5 example are connected in series. One of the pre-amps (in the instant example the second one 520) has a variable gain and so can be used to control the power level of microwaves output by the apparatus. The gain of the variable gain pre-amp 520 is controlled by the controller 101. Preferably the variable gain pre-amp is configured to operate only in its linear regions, but if a look-up table or similar software function is provided to convert low-level input power demands to a representative bias voltage then it may operate outside its linear region of operation.

Figure 6:
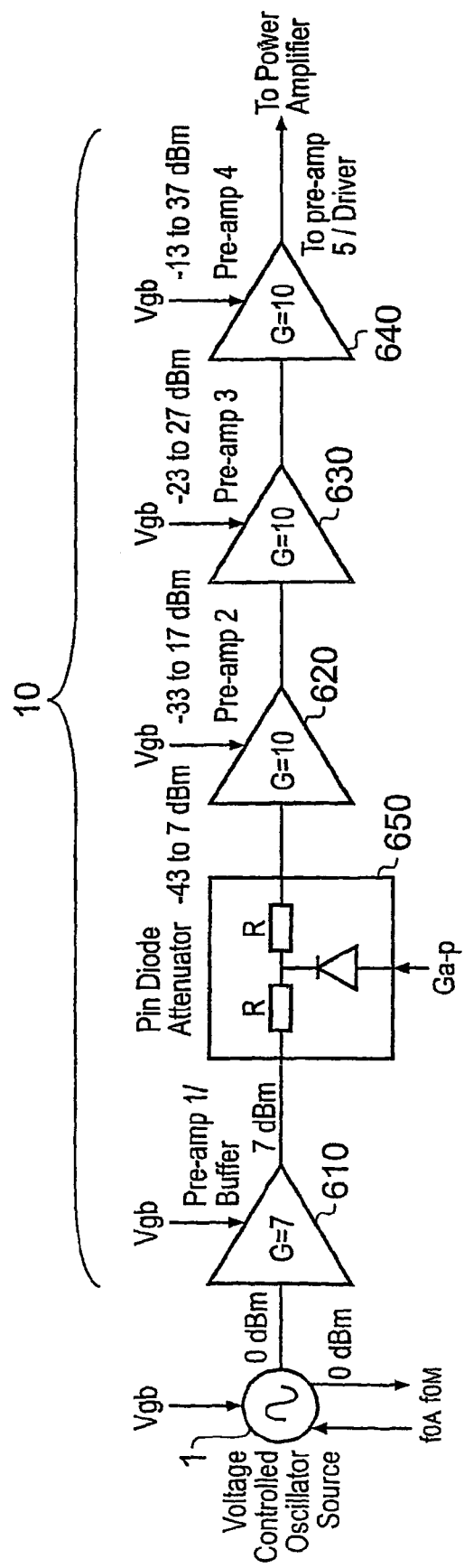
FIG. 6 shows an alternative source and pre-amplifier stage arrangement.

An example of an alternative configuration is shown in FIG. 6. There are a plurality of pre-amps 610, 620, 630 and 640 as in the FIG. 5 example, but the power level controller is a pin diode attenuator 650 (which in turn is controlled by the controller 101). The pin diode attenuator 650 is placed between two of the pre-amps, which are connected in series.

In the FIG. 6 example the pin diode attenuator 560 is placed between the first 610 and second 620 pre-amp. The pin diode attenuator 560 may be a reflective pin diode attenuator or a absorbative type attenuator.

The type and gain of the pre-amps are chosen according to the desired system requirements. Miniature Monolithic Integrated Circuit (MMICs) type pre-amps may be suitable. In one embodiment there are four pre-amps, the first having a gain of 7 dB and the others 10 dB each.

The source of microwave radiation 1, the pre-amplifier stage 2 and the power amplifier stage 3 may be combined as one unit, e.g. on a microstrip circuit board to make the apparatus compact.

Triple Stub Tuner and Stub Actuators

It is preferred that the impedance adjuster 50 is a stub tuner.

FIG. 7 shows a suitable triple stub tuner. The triple stub tuner 730 comprises a waveguide having two closed ends, an input 731, an output 732 and three tuning stubs 740, 750, 760. Each tuning stub 740, 750, 760 is positioned in a respective aperture 741, 751, 761 in a wall of the waveguide and is moveable to vary the depth to which it extends into the waveguide. By varying the depth to which each stub extends into the waveguide it is possible to adjust the impedance of the impedance adjuster. In this way the impedance of the ablation apparatus 100, 200 can be matched to that of the tissue 6 to be ablated. Although the triple stub tuner shown in FIG. 7 is circular in cross-section (see FIG. 8), it would be possible to have one rectangular or square in cross-section.

In this embodiment an actuator (not shown in FIG. 7), such as a servomotor or piezoelectric device, controls the depth of each tuning stub 740, 750, 760. The actuator is controlled by the controller 101 on the basis of the magnitude and phase detected by the detectors and/or the user interface 110.

The apertures 741, 751 and 761 may be in different walls or the same wall of the waveguide as shown in FIG. 7.

The waveguide 730 of the triple stub tuner shown in FIG. 7 has an input side and an output side. The input side and the output side are D.C. (direct current) isolated from each other by a D.C. insulator 770. The insulator 770 allows passage of the frequencies of interest (those generated by the source of microwave radiation, e.g. 14-14.5 GHz) but blocks D.C. Any suitable insulator may be used, Kapton tape or a thin sheet of low loss, high voltage breakdown dielectric material such as PTFE or polypropylene are two possibilities. Preferably the insulation is good up to 6 KV.

In the FIG. 7 example the waveguide 730 comprises two cylinders—one on the input side and one of the output side—which are fitted together one inside the other in a close fit and separated by the insulator 770. It is possible to separate the two cylinders which facilitates setting up and adjustment of the input and output probes 710 and 720.

The input and outputs 710 and 720 may conveniently be in the form of E-field probes extending into the waveguide. They may have type n-connectors for connection to the rest of the apparatus. H-field probes may also be used, as could SMA connectors.

The waveguide 730 is preferably cylindrical in cross-section as shown in FIG. 8 which is a cross-section along the line A-A of FIG. 7 and also shows the (laterally off-set) adjustable tuning stub 740.

In FIG. 7 the tuning stubs are placed one three eights of a wavelength (of the microwave radiation generated by the source, or the average of its band) apart; in alternative embodiments they may be placed one eighth or five eighths wavelength apart—other suitable distances may be apparent to a person skilled in the art.

Figure 21:
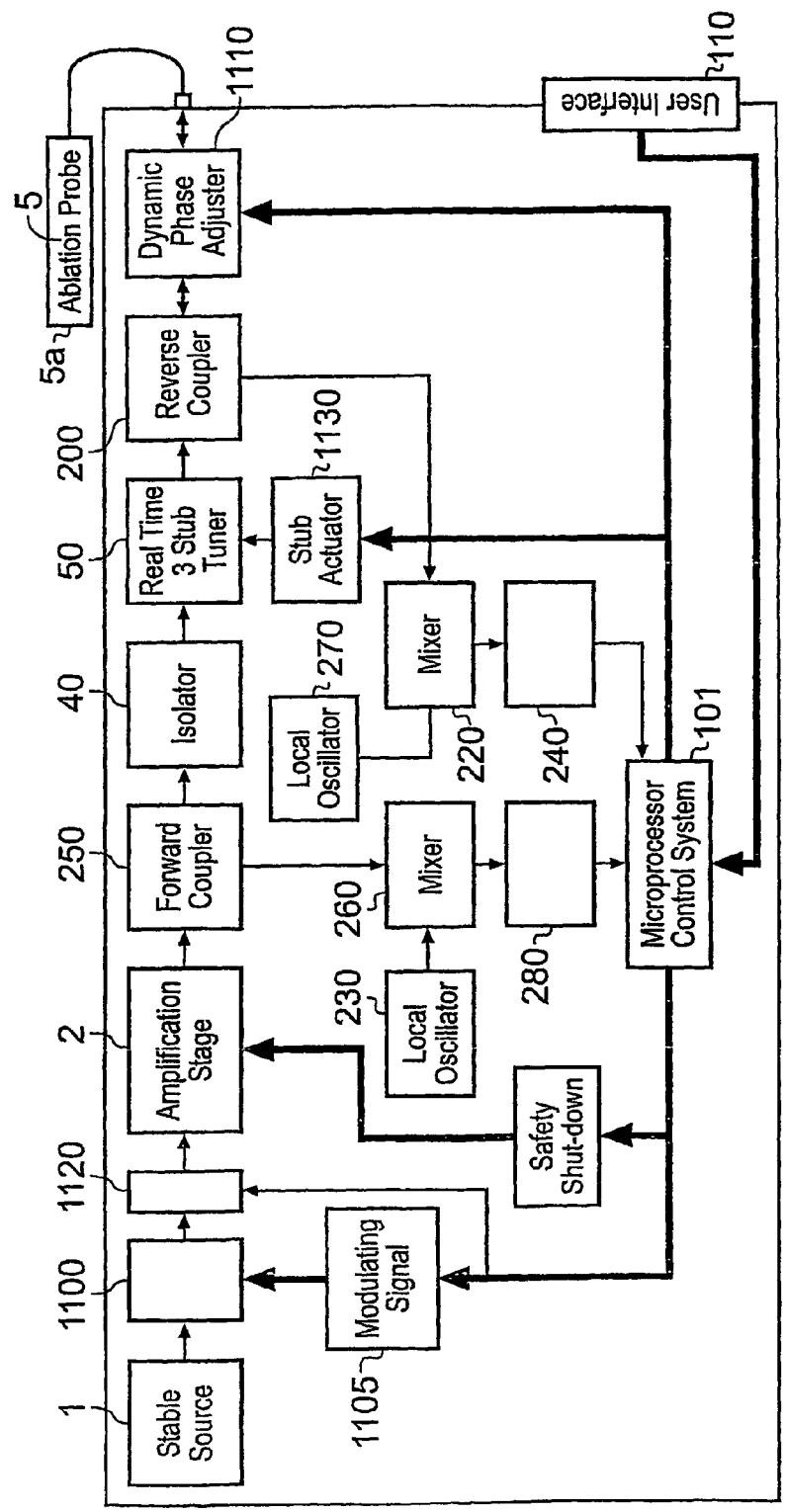
FIG. 21 shows an alternative embodiment having a modulator.

FIG. 21 shows an alternative embodiment of the apparatus in which like reference numerals indicate like parts to those described previously. Only the new features will be described below, as the others have been described previously. A modulator 1100 and a filter 1120 are provided between the source of microwave radiation 1 and the amplifying system 2. The modulator 1100 is controlled by a modulating signal 1105 from the controller 101 to which it is connected. When it is in an ON state the modulator 1100 modulates the microwave radiation from the source 1 into pulses having a frequency in the range 10 kHz to 500 MHz inclusive. The modulator 1100 is flexible and capable of modulating to any frequency within this range, the frequency modulated being selected by the controller 101. The filter 1120 is connected to the output of the modulator 1100 and the input of the amplifying system 2. It is controlled by the controller 101. When the modulator 1100 is in an ON state the filter 1120 is controlled to filter out the higher microwave frequencies from the source 1, so that only a wave form having a frequency of the modulation pulses is passed. Thus, when the modulator 1100 is in its ON state radiation having a selected frequency in the range 10 kHz to 500 MHz is output to the rest of the apparatus and through the probe 5. Radiation of this frequency is particularly suitable for cutting. When the modulator 1100 is in an OFF state, the microwave radiation from the source 1 is not modulated and the filter 1120 passes the microwave radiation, so that microwave radiation is output to the rest of the apparatus and the probe 5. Microwave radiation is particularly effective for ablating cancerous tissue. It is preferred that the modulation frequency, when the modulator is in the ON state is a frequency in the range 500 kHz to 30 MHz, as these frequencies have been found even more suitable for cutting of tissue because they are high enough that nerve stimulation is not produced but low enough that thermal margins are kept to a minimum.

FIG. 21 embodiment uses a 3 stub tuner as the impedance adjuster. A stub actuator 1130 is configured to control the stubs, so as to adjust the output impedance of the impedance adjuster, and is controlled by the controller 101 on the basis of the power and phase detected by the detectors 230, 250, 260, 280 and 200, 220, 240 and 270. Note that in FIG. 21 embodiment a separate local oscillators 230, 270 are used for the forward and reflected microwave radiation detectors.

A phase adjustor 1110 is provided between the impedance adjuster 50 and the probe 5. The phase adjuster 1110 is controllable by the controller 101 to make the effective distance between the output of the impedance adjuster 50 and the distal end 5a of the probe 5 to be equal to a multiple of the wavelength of the microwave radiation produced by the source divided by two. As discussed previously this is advantageous for impedance matching and minimising the amount of reflected radiation.

As will be apparent to a person skilled in the art one or both of the modulator and the phase adjustor could be used in any one of the other embodiments described above.

Probes

The part of the ablation apparatus generally designated 100 in FIG. 1 may be used with many different types of probe 5. Accordingly the apparatus preferably has a probe detector that is capable of detecting the type of probe which is connected. The probe may have a device for sending an identifying signal to the probe detector. The probe detector may be part of the controller 101. The controller is configured to display probe type and procedural information relating to the detected probe, it may also be configured to vary the power level according to the probe type.

Figure 9:
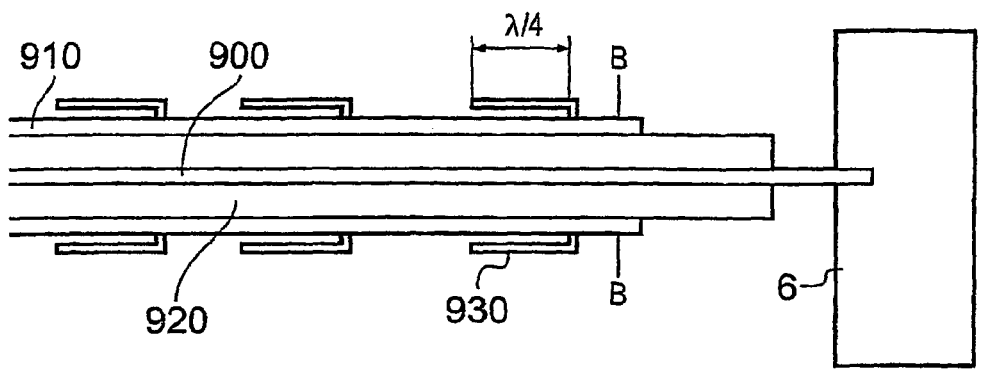
FIG. 9 shows a coaxial probe being inserted into some tissue.
Figure 10:
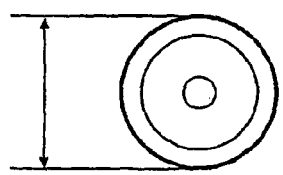
FIG. 10 is a cross-sectional view of the coaxial probe of FIG. 9 along the line B-B.

Various Probes Will Now be Described:

FIG. 9 shows a co-axial probe having a first conductor 900, a second conductor 910 and a dielectric 920 between the two. The first conductor 900 is of thin elongate form and is made of a highly conductive material such as silver or copper. The second conductor 920 is coaxial with the first and forms an outer conducting sheath. The dielectric is a low loss material for microwave frequencies. The characteristic impedance of the probe is determined by the ratio of the inner diameter of the second conductor 910 to the outer diameter of the first conductor 900. The dielectric 930 extends out of the conducting sheath 920 and the first conductor 900 extends further out of the dielectric and can be used to penetrate tissue 6. FIG. 10 is a cross-section along the line B-B of FIG. 9.

The probe of FIG. 9 has a plurality of baluns 930. Each balun is in the form of a third conductor surrounding a portion of the outer conductor 920. Each balun 930 is in conductive contact with the second conductor 910 at one end and insulated by air from second conductor for the rest of its length. Each balun has a length of one quarter of the wavelength or odd multiples thereof used by the apparatus. The baluns minimise the return current along the second conductor and thus help to minimise the risk of shock to the patient or the operator, and to reduce or eliminate the heating of healthy tissue.

Figure 11:
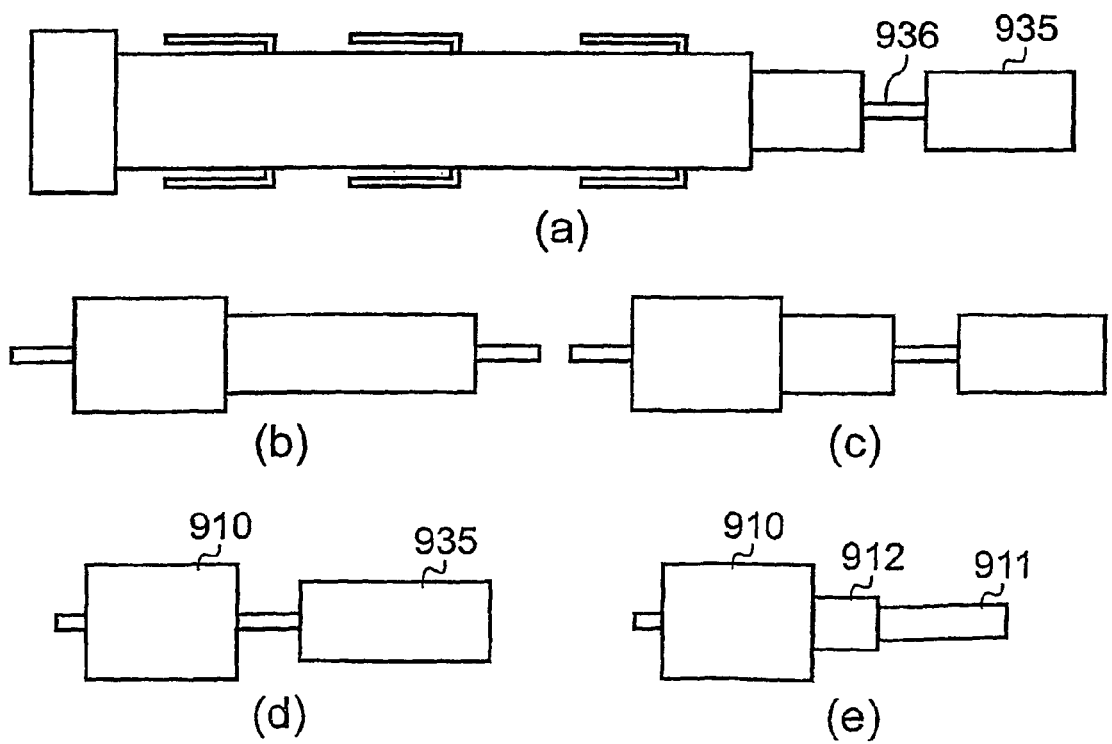
FIGS. 11*a*-11*e* show different types of possible end structures for the probe.

FIG. 11(a) shows a probe similar to that of FIG. 9, except that the first conductor 900 as a further piece of dielectric material 935 at its end (preferably the dielectric 935 is the same material as the dielectric 920). Only a portion 936 of the first conductor between the two pieces of dielectric material 920, 935 is exposed.

FIG. 11(b) is a close up view of the end of the probe of FIG. 9. FIG. 11(c) is a close up view of the end of the probe of FIG. 11(a). FIG. 11(d) shows a variant in which the first conductor has a dielectric 935 at its tip end, but the first piece of dielectric 920 does not extend out of the conductive sheath 910. Thus the portion of the first conductor between the sheath 910 and the second dielectric 935 is exposed. FIG. 11(e) shows a variation in which the dielectric 920 does not extend out of the sheath 910, and the first conductor terminates in a tungsten needle 911 having a metal ferrule 912 surrounding a portion proximate the end of the sheath 910.

Figure 12:
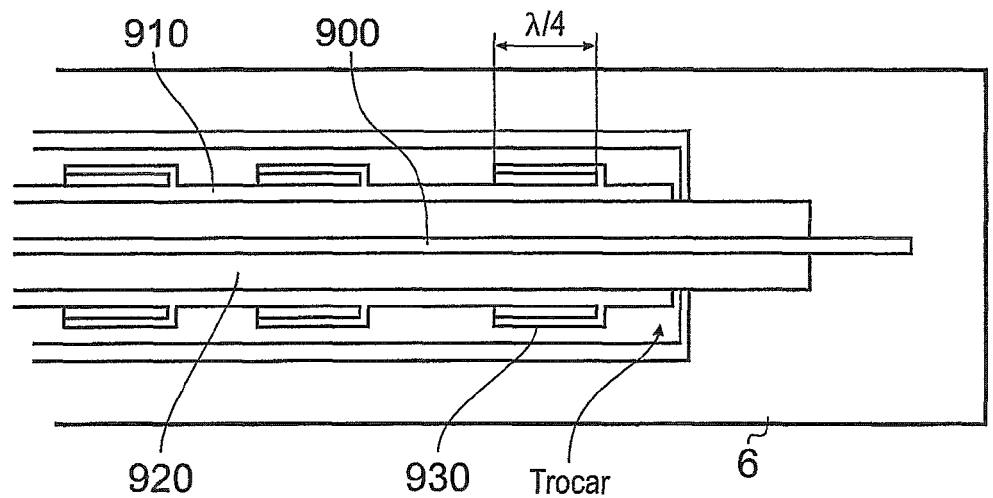
FIG. 12 shows a coaxial probe inserted into tissue.
Figure 13:
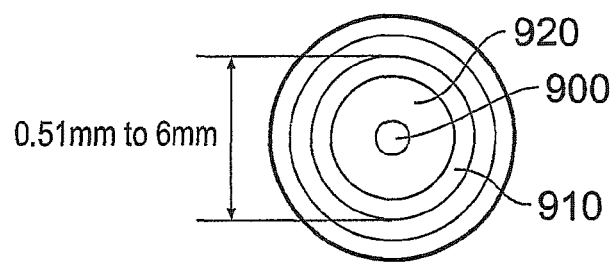
FIG. 13 is a cross-sectional view along the line C-C of FIG. 12.

FIG. 12 shows a coaxial probe inserted into tissue 6. The same reference numerals indicate like parts as in FIG. 9. The second conductor 910 and baluns 930 are surrounded by a trocar, which is a tube inserted into the body that allows a probe or other device such as an endoscope to be inserted. FIG. 13 is a cross-section along the line C-C of FIG. 12.

Figure 14:
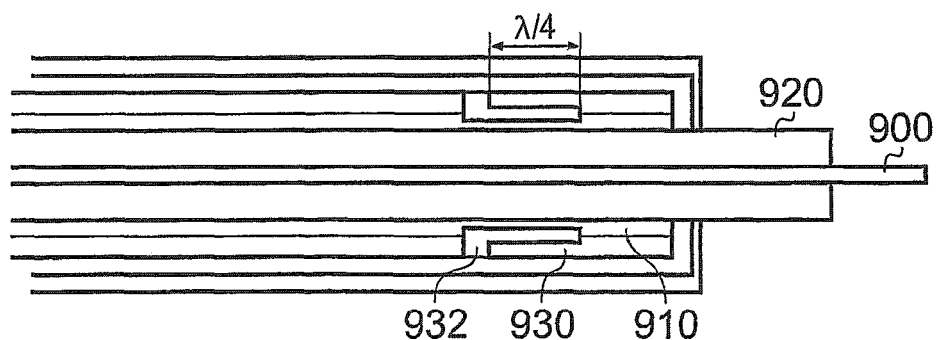
FIG. 14 shows a coaxial probe having baluns formed by a particular technique.

FIG. 14 shows an alternative embodiment of the probe in which a balun is formed by spraying dielectric 932 between second and third conductors 910, 930. Dielectric—cast 235D from Cumming Corporation is a particularly suitable dielectric for this purpose. One or more baluns may be formed in this way. The length of the balun is one-quarter wavelength or odd multiples thereof.

In an alternative embodiment the baluns may be a pure dielectric baluns with no third conductor 930. Appropriate modifications will be apparent to a person skilled in the art.

Figure 15:
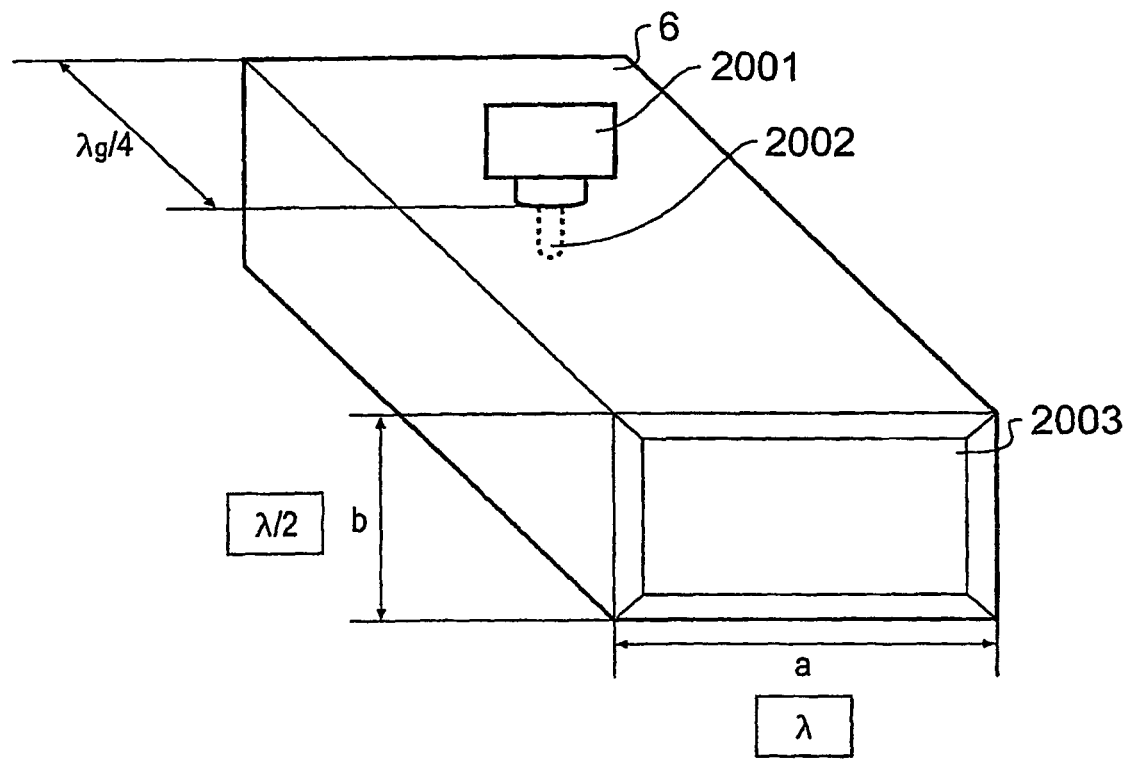
FIG. 15 shows a probe in the form of a rectangular waveguide.

FIG. 15 shows a rectangular waveguide probe having a depth of one half wavelength and a width of one wavelength. With this configuration the $Te_{21}$ mode propagates. Microwaves are coupled into the ablation probe 6 via an E-field probe 2002 extending into the waveguide and having a type N or type K or SMA connector 2001. The waveguide aperture 2003 is filled (loaded) with a low loss dielectric.

Figure 22:
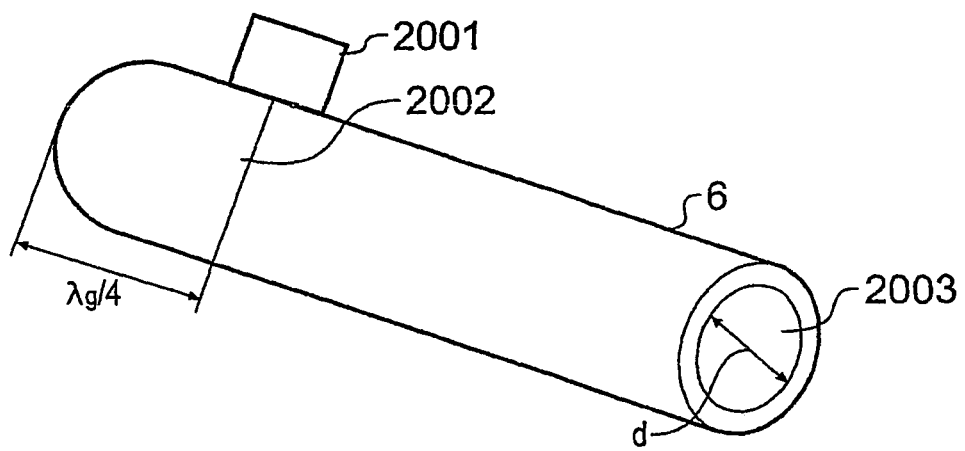
FIG. 22 shows a probe in the form of a cylindrical waveguide.

FIG. 22 shows a cylindrical waveguide ablation probe 6, the central aperture 2003 of which is filled with a solid dielectric material. It has an E-field probe with an SMA, N or K type connector λ/4 away from one of its ends. H-field probes could also be used.

In both FIG. 14 and FIG. 15 the waveguide housing (walls) are formed of copper, brass or aluminium and the input (E-field probe) is positioned one-quarter wavelength from one end of the waveguide.

Figure 23:
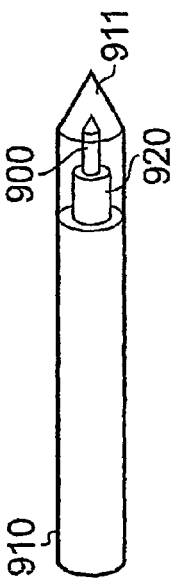
FIG. 23 shows a probe with a ceramic tip.

FIG. 23 shows an elongate ablation probe having a ceramic tip 911 at its distal end. The tip is configured to deliver microwave radiation into tissue. The ceramic is a low loss microwave ceramic material having a relative permittivity ($\in_r$) of 6.5 at microwave frequencies.

The invention claimed is:

1. A tissue ablation apparatus for ablating tissue comprising:
   a phase-locked source of microwave radiation having a stable output frequency in the range of 5 to 60 GHz;
   a probe connected to said phase-locked source, said probe having a low loss ceramic tip at a distal end thereof, the ceramic tip being configured for directing said microwave radiation into said tissue to be ablated;
   a local oscillator for producing a signal, having a frequency different from said frequency of said microwave radiation;
   a first detector for detecting the magnitude and phase of a reflected portion of said microwave radiation reflected back through said probe towards said phase-locked source;
   said first detector being connected to the local oscillator and configured to determine the magnitude and phase of said reflected portion of said microwave radiation by comparing said reflected portion of said microwave radiation with said signal produced by said local oscillator; and
   an impedance adjuster connected between said phase-locked source of microwave radiation and said probe, said impedance adjuster having an adjustable complex impedance that is controllable based on said determined magnitude and phase of said reflected portion of said microwave radiation.

2. An apparatus according to claim 1 further comprising a second detector for detecting the magnitude and phase of forward directed microwave radiation directed from said phase-locked source toward said probe, said second detector being connected to said local oscillator or a different local oscillator, the second detector being configured to determine the magnitude and phase of said forward directed microwave radiation by comparing it with a signal produced by said or said different local oscillator, and wherein said adjustable complex impedance of the impedance adjuster is further controllable based on said determined magnitude and phase of said forward directed microwave radiation.

3. An apparatus according to claim 2 further comprising a third detector for detecting the magnitude and phase of either forward directed microwave radiation or reflected microwave radiation, said third detector being connected to said local oscillator or a different local oscillator, the third detector being configured to determine the magnitude and phase of either said forward directed microwave radiation or said reflected microwave radiation by comparing it with a signal produced by said or said different local oscillator, and wherein said adjustable complex impedance of the impedance adjuster is further controllable based on said determined magnitude and phase of either said forward directed microwave radiation or said reflected microwave radiation.

4. An apparatus according to claim 1 wherein said first detector comprises a mixer for mixing the signal from said local oscillator with said reflected portion of said microwave radiation.

5. An apparatus according to claim 1 wherein said first detector comprises a power sensor and a phase comparator connected to said local oscillator.

6. An apparatus according to claim 1 wherein said local oscillator is separate from said phase-locked source of microwave radiation.

7. An apparatus according to claim 1 wherein said local oscillator is connected to said phase-locked source of microwave radiation and configured to produce a signal derived from said phase-locked source, but having a different frequency to the frequency of said phase-locked source of microwave radiation.

8. An apparatus according to claim 1 further comprising a controller for automatically adjusting said adjustable complex impedance of said impedance adjustor on the basis of the magnitude and phase of said radiation detected by said detector.

9. An apparatus according to claim 8 wherein said controller is configured to adjust said adjustable complex impedance dynamically in response to the variation in the magnitude and phase of said radiation detected by said detector.

10. An apparatus according to claim 1 wherein the ceramic tip of said probe is configured to penetrate biological tissue.

11. An apparatus according to claim 1 further comprising a separator for separating said reflected portion of said microwave radiation from forward directed microwave radiation being directed towards said probe.

12. An apparatus according to claim 7 wherein said impedance adjuster is a stub tuner.

13. An apparatus according to claim 1 wherein the probe is coaxial.

14. An apparatus according to claim 1 wherein the probe is a waveguide.

15. An apparatus according to claim 1 wherein the probe has an outer diameter of less than 1 mm.

16. A microwave tissue ablation apparatus according to claim 1 wherein the phase-locked source of microwave radiation produces radiation of wavelength $\lambda$, and a radiation channeling means for conveying microwave radiation connects said impedance adjuster and said probe, said channeling means having an adjustable length whereby the combined length of said channeling means and said probe can be adjusted to be equal to a multiple of $\lambda/2$.

17. A method of ablating tissue comprising the steps of:
using a phase-locked source of microwave radiation to provide microwave radiation having a stable output frequency in the range of 5 to 60 GHz;
placing a probe in contact with or inserting a probe into biological tissue, the probe having a low loss ceramic tip at a distal end thereof;
directing said microwave radiation through the ceramic tip of said probe into the tissue to ablate the tissue;
detecting the magnitude and phase of a reflected portion of said microwave radiation reflected back through the probe by using a first detector and a local oscillator, the local oscillator producing a signal having a frequency different from said frequency of said microwave radiation and the first detector operating to determine the magnitude and phase of said reflected portion of said microwave radiation by comparing said reflected portion of said microwave radiation with said signal produced by said local oscillator, and
adjusting the complex impedance of an impedance adjustor connected between said phase-locked source and said probe on the basis of the magnitude and phase of the microwave radiation detected by said first detector.

18. A method of ablating tissue comprising the steps of:
using a phase-locked source of microwave radiation to provide microwave radiation having a stable output frequency in the range of 5 to 60 GHz;
placing a probe in contact with or inserting a probe into biological tissue, the probe having a low loss ceramic tip at a distal end thereof;
directing said microwave radiation from said phase-locked source through an impedance adjuster and then through the ceramic tip of said probe into said tissue to ablate the tissue; said impedance adjustor having an input connected to said phase-locked source and an output connected to said probe, said input and said output having respective complex impedances;
detecting the magnitude and phase of a reflected portion of said microwave radiation that is reflected back through said probe towards the phase-locked source by using a first detector and a local oscillator; said local oscillator generating a signal having a frequency different from said frequency of said microwave radiation, said first detector using said local oscillator signal in combination with the reflected radiation or a signal derived from said reflected radiation to determine the magnitude and phase of said reflected radiation; and
adjusting said complex impedance of said output of said impedance adjustor on the basis of said magnitude and phase of said reflected microwave radiation detected by said first detector, so as to minimize the amount of microwave radiation which is reflected back through said probe.

19. A method according to claim 17 wherein the probe is inserted into the tissue so that an end of the ceramic tip of the probe is proximate to or inside a cancerous tumor in the tissue and microwave radiation is then passed through the ceramic tip of the probe to ablate said cancerous tumor.

20. A method according to claim 19 wherein the microwave radiation is used to cut a path in the tissue so that the probe can be inserted near to or into said tumor.

21. A method according to claim 18 wherein the magnitude and phase of forward directed microwave radiation directed toward said probe from said phase-locked source of microwave radiation is detected by using a second detector and said local oscillator or a different local oscillator, and said adjustable complex impedance of said impedance adjuster is adjusted based on the signal magnitudes and phases detected by said first and second detectors.

22. A method according to claim 21 wherein a third detector is used to detect the magnitude and phase of either forward directed or reflected radiation and said adjustable complex impedance of said impedance adjustor is adjusted on the basis of information provided by said first, second and third detectors.

23. A method according to claim 17 wherein said adjustable complex impedance of said impedance adjuster is adjusted automatically by a control means on the basis of said magnitude and phase detected by said detector so as to minimize the amount of microwave radiation reflected back through said probe.

24. A method according to claim 23 wherein said impedance adjustment is carried out dynamically as the detected magnitude and phase varies.

25. A microwave tissue ablation apparatus according to claim 1 wherein the phase-locked source of microwave radiation is phase locked to a stable reference signal having a single frequency.

26. A microwave tissue ablation apparatus according to claim 25 wherein the phase-locked source is tunable so that its stable output frequency can be varied in a controlled manner.

27. A microwave tissue ablation apparatus according to claim 1 including a microwave amplifying system connected between the phase-locked source and the probe, the microwave amplifying system comprising a solid state power amplifier connected to receive at an input thereof the microwave radiation from the phase-locked source.

28. An apparatus as claimed in claim 1, wherein the stable output frequency of said phase-locked source is in the range of 13 to 60 GHz.

29. An apparatus as claimed in claim 10, wherein said probe further includes:
an outer cylindrical conductor having a distal end;
an inner cylindrical conductor mounted coaxially in said outer conductor and terminating in a distal end which extends from the distal end of the outer conductor; and
a dielectric between said inner cylindrical conductor and said outer cylindrical conductor and terminating in a distal end which is intermediate the distal end of said outer cylindrical conductor and the distal end of said inner cylindrical conductor; and
wherein said ceramic tip of said probe extends from the distal end of said outer cylindrical conductor and surrounds said dielectric and said inner cylindrical conductor.

30. An apparatus as claimed in claim 29,
wherein said ceramic tip of said probe is cone shaped and terminates in a pointed end for penetration into biological tissue; and
wherein said distal end of said inner cylindrical conductor includes a cone shaped end which is located at least partially inside of the cone shaped end of said ceramic tip.

31. A method as claimed in claim 17, wherein the stable output frequency of said phase-locked source is in the range of 13 to 60 GHz.

32. A method as claimed in claim 17, wherein said probe includes:
an outer cylindrical conductor having a distal end;
an inner cylindrical conductor mounted coaxially in said outer conductor and terminating in a distal end which extends from the distal end of the outer conductor; and
a dielectric between said inner cylindrical conductor and said outer cylindrical conductor and terminating in a distal end which is intermediate the distal end of said outer cylindrical conductor and the distal end of said inner cylindrical conductor; and
wherein the ceramic tip of said probe extends from the distal end of said outer cylindrical conductor and surrounds said dielectric and said inner cylindrical conductor.

33. A method as claimed in claim 32,
wherein the ceramic tip of said probe is cone shaped and terminates in a pointed end for penetration into biological tissue; and
wherein said distal end of said inner cylindrical conductor includes a cone shaped end which is located at least partially inside of the cone shaped end of said ceramic tip.

34. A method as claimed in claim 18, wherein the stable output frequency of said phase-locked source is in the range of 13 to 60 GHz.

35. A method as claimed in claim 18, wherein said probe includes:
an outer cylindrical conductor having a distal end;
an inner cylindrical conductor mounted coaxially in said outer conductor and terminating in a distal end which extends from the distal end of the outer conductor; and
a dielectric between said inner cylindrical conductor and said outer cylindrical conductor and terminating in a distal end which is intermediate the distal end of said outer cylindrical conductor and the distal end of said inner cylindrical conductor; and
wherein the ceramic tip of said probe extends from the distal end of said outer cylindrical conductor and surrounds said dielectric and said inner cylindrical conductor.

36. A method as claimed in claim 35,
wherein the ceramic tip of said probe is cone shaped and terminates in a pointed end for penetration into biological tissue; and
wherein said distal end of said inner cylindrical conductor includes a cone shaped end which is located at least partially inside of the cone shaped end of said ceramic tip.

* * * * *